US012226558B2

United States Patent
Rohde

(10) Patent No.: US 12,226,558 B2
(45) Date of Patent: *Feb. 18, 2025

(54) DIALYSIS SYSTEM INCLUDING A WATER TREATMENT DEVICE

(71) Applicants: Baxter International Inc., Deerfield, IL (US); Baxter Healthcare SA, Glattpark (CH)

(72) Inventor: Justin B. Rohde, Des Plaines, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/878,680

(22) Filed: Aug. 1, 2022

(65) Prior Publication Data

US 2022/0362446 A1 Nov. 17, 2022

Related U.S. Application Data

(63) Continuation of application No. 15/825,878, filed on Nov. 29, 2017, now Pat. No. 11,400,192, which is a (Continued)

(51) Int. Cl.
*A61M 1/16* (2006.01)
*A61M 5/44* (2006.01)
(Continued)

(52) U.S. Cl.
CPC .......... *A61M 1/1656* (2013.01); *A61M 1/166* (2014.02); *A61M 5/44* (2013.01);
(Continued)

(58) Field of Classification Search
CPC ...... A61M 1/1656; A61M 1/166; A61M 5/44; A61M 2205/3553; A61M 2205/502;
(Continued)

(56) References Cited

U.S. PATENT DOCUMENTS

| 5,236,476 A | 8/1993 | Klick |
| 5,259,954 A | 11/1993 | Taylor |

(Continued)

FOREIGN PATENT DOCUMENTS

| DE | 19605260 | 11/1996 |
| EP | 1614437 | 1/2006 |

(Continued)

OTHER PUBLICATIONS

Final Office Action for related Japanese Application No. 2021-008641; action dated Aug. 2, 2022; (3 pages).

(Continued)

*Primary Examiner* — Rebecca M Fritchman
(74) *Attorney, Agent, or Firm* — K&L Gates LLP

(57) ABSTRACT

A dialysis system is disclosed. An example dialysis system includes a water treatment device configured to provide purified water and a dialysis machine including a dialysate holding tank, and a dialysate mixing pump connected to a source of concentrate. The dialysis machine is configured to prepare dialysate using the purified water by receiving an indication that a batch of dialysate is needed, transmitting a first message to the water treatment device to begin providing the purified water, and causing the dialysate mixing pump to pump a concentrate from the source of concentrate for mixing with the purified water to form the dialysate for storage in the dialysate holding tank. After the batch of the dialysate has been stored to the dialysate holding tank, the dialysis machine transmits a second message to the water treatment device to stop providing the purified water.

17 Claims, 15 Drawing Sheets

Related U.S. Application Data continuation of application No. 13/828,822, filed on Mar. 14, 2013, now Pat. No. 10,973,968, which is a continuation-in-part of application No. 13/494,259, filed on Jun. 12, 2012, now Pat. No. 8,419,933, which is a continuation of application No. 13/030,909, filed on Feb. 18, 2011, now Pat. No. 8,216,452, which is a continuation of application No. 12/031,605, filed on Feb. 14, 2008, now Pat. No. 7,892,423.

(51) Int. Cl.
*G16H 40/63* (2018.01)
*G16H 20/40* (2018.01)
*G16H 40/67* (2018.01)

(52) U.S. Cl.
CPC ..... *G16H 40/63* (2018.01); *A61M 2205/3553* (2013.01); *A61M 2205/502* (2013.01); *G16H 20/40* (2018.01); *G16H 40/67* (2018.01)

(58) Field of Classification Search
CPC ........ G16H 40/63; G16H 20/40; G16H 40/67; G06F 19/3406; G06F 19/3481
USPC .......................................................... 210/143
See application file for complete search history.

(56) References Cited

U.S. PATENT DOCUMENTS

| | | | |
|---|---|---|---|
| 5,274,434 A | 12/1993 | Morioka et al. | |
| 5,658,456 A | 8/1997 | Kenley et al. | |
| 6,280,634 B1* | 8/2001 | Shah | A61M 1/3629 210/746 |
| 6,582,385 B2 | 6/2003 | Burbank et al. | |
| 6,861,033 B2 | 3/2005 | Mullins et al. | |
| 7,419,587 B2 | 9/2008 | Valbjoern et al. | |
| 7,544,300 B2 | 6/2009 | Brugger et al. | |
| 7,749,393 B2 | 7/2010 | Brugger et al. | |
| 7,892,423 B2 | 2/2011 | Rohde et al. | |
| 7,976,711 B2 | 7/2011 | Brugger et al. | |
| 8,071,055 B2 | 12/2011 | Newcombe | |
| 8,177,977 B2 | 5/2012 | Gaignet | |
| 8,192,387 B2 | 6/2012 | Brugger et al. | |
| 8,216,452 B2 | 7/2012 | Rohde et al. | |
| 8,246,826 B2 | 8/2012 | Wilt et al. | |
| 8,354,029 B2 | 1/2013 | Hank | |
| 8,357,298 B2 | 1/2013 | Demers et al. | |
| 8,409,441 B2 | 4/2013 | Wilt et al. | |
| 8,425,767 B2 | 4/2013 | Fava et al. | |
| 2003/0135250 A1 | 7/2003 | Lauman et al. | |
| 2003/0220605 A1 | 11/2003 | Bowman et al. | |
| 2008/0045877 A1 | 2/2008 | Evin et al. | |
| 2008/0097283 A1* | 4/2008 | Plahey | A61M 1/28 604/29 |
| 2008/0210606 A1 | 9/2008 | Burbank | |
| 2009/0008318 A1 | 1/2009 | Anes et al. | |
| 2009/0008331 A1* | 1/2009 | Wilt | A61M 1/3649 210/321.71 |
| 2009/0045121 A1 | 2/2009 | Kabayama et al. | |
| 2009/0182263 A1* | 7/2009 | Burbank | A61J 1/2003 210/767 |
| 2009/0218285 A1* | 9/2009 | Hank | B01D 65/104 210/85 |
| 2010/0018923 A1 | 1/2010 | Rohde et al. | |
| 2010/0051546 A1 | 3/2010 | Vuong et al. | |
| 2010/0078092 A1 | 4/2010 | Weilhoefer et al. | |
| 2010/0137693 A1 | 6/2010 | Porras et al. | |
| 2010/0326916 A1 | 12/2010 | Wrazel et al. | |
| 2010/0332149 A1 | 12/2010 | Scholpp | |
| 2011/0100913 A1 | 5/2011 | Minami et al. | |
| 2011/0180480 A1 | 7/2011 | Kloeffel et al. | |
| 2011/0186521 A1 | 8/2011 | Burbank et al. | |
| 2011/0192796 A1 | 8/2011 | Smejtek et al. | |
| 2011/0315611 A1 | 12/2011 | Fulkerson et al. | |
| 2012/0138533 A1 | 6/2012 | Curtis et al. | |
| 2013/0008854 A1 | 1/2013 | Wallace et al. | |
| 2013/0020237 A1 | 1/2013 | Wilt et al. | |
| 2014/0238912 A1 | 8/2014 | Vincent | |
| 2016/0058933 A1* | 3/2016 | Ballantyne | G06F 21/565 210/85 |

FOREIGN PATENT DOCUMENTS

| | | |
|---|---|---|
| EP | 2180908 | 5/2010 |
| EP | 2181965 | 5/2010 |
| JP | 2003513714 | 4/2003 |
| JP | 2003199719 | 7/2003 |
| JP | 2005503179 | 2/2005 |
| JP | 2008-23324 A | 2/2008 |
| JP | 2010-279423 A | 12/2010 |
| JP | 2012530577 | 12/2012 |
| WO | 96/25214 | 8/1996 |
| WO | 9640318 | 12/1996 |
| WO | 2012/120078 | 4/2003 |
| WO | 2007118235 | 10/2007 |
| WO | 2007/148442 A1 | 12/2007 |
| WO | 2008-138311 | 11/2008 |
| WO | 2011/069110 | 6/2011 |
| WO | 2012/129501 | 9/2012 |
| WO | WO2012/129501 A2 | 9/2012 |
| WO | 2013/173349 A2 | 11/2013 |

OTHER PUBLICATIONS

European Communication dated Mar. 2, 2015 for Application No. 09 710 209.9-1662, 6 pages.
Office Action for Mexican Patent Application No. Mx/a/2010/008961 received Jul. 1, 2013.
Manns et al., The Acu-men TM: A new device for continuous renal replacement therapy in acute renal failure, Kidney International, 1998, pp. 268-275, vol. 54.
Search and Examination Report dated Jul. 29, 2014 for related GB Appln. No. 1322331.8.
European Search Report—EP Application No. 16 17 6496 dated Mar. 21, 2017—10 pages.
U.S. Appl. No. 60/903,582, filed Feb. 27, 2007.
U.S. Appl. No. 60/904,024, filed Feb. 27, 2007.
U.S. Appl. No. 61/092,239, filed Aug. 27, 2008.
U.S. Appl. No. 61/489,544, filed May 24, 2011.
U.S. Appl. No. 61/489,394, filed Jun. 17, 2011.
U.S. Appl. No. 62/003,374, filed May 27, 2014.
U.S. Appl. No. 62/004,567, filed May 29, 2014.
Search Report issued in French application No. 1452117, dated Mar. 31, 2016, 2 pages.
Written Opinion issued in French application No. 1452117, dated Mar. 31, 2016, 5 pages.
Notice of Reasons for Rejection mailed on Dec. 5, 2017 in corresponding JP Application No. 2013-257132.
German Office Action for related German Application No. 102014204546.0; action dated Apr. 24, 2018; (12 pages).
Japanese Office Action for related Japanese Application No. 2013-257132; action dated Aug. 14, 2018; (4 pages).
Mexican Office Action and English translation for related Mexican Application No. MX/a/2014/001566; action forwarded Nov. 6, 2018; (6 pages).
Canadian Office Action for application No. 2836575, dated Nov. 13, 2019—4 pages.
Japanese Office Action for related Japanese Application No. 2018-233707; action dated Sep. 23, 2020; (4 pages).
Mexican Office Action and English translation for related Mexican Application No. MX/a/2019/001526; action forwarded Dec. 10, 2021; (7 pages).
Japanese Office Action for related Japanese Application No. 2021-008641; action dated Jan. 11, 2022; (15 pages).
Office Action for related Japanese Application No. 2019-571624; report dated Mar. 22, 2022; (14 pages).
Office Action received in related application No. 20 180 920.9-1122, dated Jun. 5, 2023.

(56) References Cited

OTHER PUBLICATIONS

JP 2022-193339 Notice of Reasons For Rejection with English language translation, dated Feb. 1, 2024 with English language translation.

* cited by examiner

DIALYSIS SYSTEM INCLUDING A WATER TREATMENT DEVICE

PRIORITY CLAIM

This application claims priority to and the benefit as a continuation application of U.S. patent application Ser. No. 15/825,878, filed Nov. 29, 2017, entitled "Peritoneal Dialysis System including a Water Treatment Device" (now U.S. Pat. No. 11,400,192), which is a continuation application of U.S. patent application Ser. No. 13/828,822, filed Mar. 14, 2013, entitled, "Control of a Water Device via a Dialysis Machine User Interface" (now U.S. Pat. No. 10,973,968), which is a continuation-in-part application of U.S. patent application Ser. No. 13/494,259, filed Jun. 12, 2012, entitled, "Dialysis System Including Multi-Heater Power Coordination" (now U.S. Pat. No. 8,419,933), which is a continuation application of U.S. patent application Ser. No. 13/030,909, filed Feb. 18, 2011, entitled, "Dialysis System Including Multi-Heater Power Coordination" (now U.S. Pat. No. 8,216,452), which is a continuation application of U.S. patent application Ser. No. 12/031,605, filed Feb. 14, 2008, entitled, "Dialysis System Including Multi-Heater Power Coordination" (now U.S. Pat. No. 7,892,423), the entire contents of each of which are incorporated herein by reference and relied upon.

BACKGROUND

The present disclosure relates generally to renal therapy systems and more specifically to systems and methods for controlling a water treatment device solely or only through a dialysis device.

Due to disease, insult or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

Hemodialysis and peritoneal dialysis are two types of dialysis therapies commonly used to treat loss of kidney function. Hemodialysis treatment uses the patient's blood to remove waste, toxins and excess water from the patient. The patient is connected to a hemodialysis machine and the patient's blood is pumped through the machine. Catheters or needles are inserted into the patient's circulatory system to connect the blood flow to and from the hemodialysis machine. Blood and dialysate are passed through a dialyzer in the hemodialysis machine. The dialyzer can include a semi-permeable membrane separating the blood and the dialysate. As blood passes through a dialyzer in the hemodialysis machine, the dialyzer removes the waste, toxins and excess water from the patient's blood. In particular, the toxins are moved osmotically from the blood across the membrane into the dialysate. The hemodialysis machine returns the blood back to the patient. A large amount of dialysate, for example about one-hundred twenty liters, is used to dialyze the blood during a single hemodialysis treatment. The spent dialysate is then discarded. Hemodialysis treatment lasts several hours and is generally performed in a treatment center about three or four times per week.

Peritoneal dialysis uses a dialysis solution or "dialysate", which is infused into a patient's peritoneal cavity through a catheter implanted in the cavity. The dialysate contacts the patient's peritoneal membrane in the peritoneal cavity. Waste, toxins and excess water pass from the patient's bloodstream through the peritoneal membrane and into the dialysate. The transfer of waste, toxins, and water from the bloodstream into the dialysate occurs due to diffusion and osmosis, i.e., an osmotic gradient occurs across the membrane. The spent dialysate drains from the patient's peritoneal cavity and removes the waste, toxins and excess water from the patient. This cycle is repeated.

There are various types of peritoneal dialysis therapies, including continuous ambulatory peritoneal dialysis ("CAPD"), automated peritoneal dialysis and continuous flow peritoneal dialysis. CAPD is a manual dialysis treatment, in which the patient connects an implanted catheter to a drain and allows a spent dialysate fluid to drain from the peritoneal cavity. The patient then connects the catheter to a bag of fresh dialysate and manually infuses fresh dialysate through the catheter and into the patient's peritoneal cavity. The patient disconnects the catheter from the fresh dialysate bag and allows the dialysate to dwell within the cavity to transfer waste, toxins and excess water from the patient's bloodstream to the dialysate solution. After a dwell period, the patient repeats the manual dialysis procedure.

In CAPD the patient performs several drain, fill, and dwell cycles during the day, for example, about four times per day. Each treatment cycle typically takes about an hour. Manual peritoneal dialysis performed by the patient requires a significant amount of time and effort from the patient. This inconvenient procedure leaves ample room for improvement and therapy enhancements to improve patient quality of life.

Automated peritoneal dialysis ("APD") is similar to CAPD in that the dialysis treatment includes a drain, fill, and dwell cycle. APD machines, however, automatically perform three to four cycles of peritoneal dialysis treatment, typically overnight while the patient sleeps. The APD machines fluidly connect to an implanted catheter. The APD machines also fluidly connect to a source or bag of fresh dialysate and to a fluid drain.

The APD machines pump fresh dialysate from the dialysate source, through the catheter, into the patient's peritoneal cavity and allow the dialysate to dwell within the cavity so that the transfer of waste, toxins and excess water from the patient's bloodstream to the dialysate solution can take place. The APD machines then pump spent dialysate from the peritoneal cavity, though the catheter, to the drain. APD machines are typically computer controlled so that the dialysis treatment occurs automatically when the patient is connected to the dialysis machine, for example, when the patient sleeps. That is, the APD systems automatically and sequentially pump fluid into the peritoneal cavity, allow for a dwell, pump fluid out of the peritoneal cavity and repeat the procedure.

As with the manual process, several drain, fill, and dwell cycles will occur during APD. A "last fill" is typically used at the end of APD, which remains in the peritoneal cavity of the patient when the patient disconnects from the dialysis machine for the day. APD frees the patient from having to manually performing the drain, dwell, and fill steps.

For patients suffering from renal diseases, frequent dialysis is a way of life. Most peritoneal dialysis patients perform dialysis once a day. Hemodialysis patients typically require dialysis several times a week. To allow patients to continue to live their lives as normally as possible, there has been an increased desire to provide home dialysis solutions. Peritoneal dialysis is typically performed at home. Hemodialysis and other blood treatment therapies, such as hemofiltration, are performed largely in centers and clinics.

Performing dialysis, whether hemodialysis or peritoneal dialysis, at home presents more challenges and complexities for patients. Typically, dialysis is performed using a dialysis device and a fluid source. The fluid source may be provided in one or more prepared solution bag or be prepared online via a water treatment device and concentrated additives. In the case of the water treatment device, the dialysis machine and the water treatment device are operated at the same time to successfully perform a therapy. Operating two machines or devices can be difficult, especially for elderly patients or immobile patients who may not be able to easily and quickly observe and/or manipulate both devices. Viewing and/or entering information on or into the two devices may prove to be cumbersome. Both the dialysis machine and the water treatment device will produce data that may be desirable to store for analysis. The data should be accurate, timely and provide a sufficient level of detail.

A need accordingly exists for a home dialysis system that integrates a water treatment device with a hemodialysis machine, such that control of both machines or devices is centralized, and such that data may flow readily to and from both machines or devices.

SUMMARY

The system and method of the present disclosure integrate the operation of a dialysis machine and a water treatment device, such that the user in essence operates the water treatment device from the dialysis machine. That is, the user interface for the water treatment device is the user interface that controls the dialysis machine. The water treatment device can have its own small user interface but primary control of the water treatment device is via the dialysis machine. It is also contemplated to transfer data from both machines to a central repository maintained by a therapy provider, provide reports of treatment data concerning both the machine and the device to clinicians, integrate with billing and ordering systems, track consumables usage and deliver consumables as needed, and service and maintain the machines on a network of the system. To this end, in one embodiment the dialysis machine is in data fluid communication with the water treatment device via Ethernet or other wired communication. The dialysis machine is in turn in communication with the system or network. In this manner, data from the water treatment device can be sent via the dialysis machine to the network or system. The system or network can likewise send operating instructions and software upgrades via the dialysis machine to the water treatment device.

The dialysis machine includes a home therapy machine, such as, but not limited to, a home hemodialysis ("HD") machine, a home peritoneal dialysis ("PD") machine, a home hemofiltration ("HF") machine, a home hemodiafiltration ("HDF") machine, and a home continuous renal replacement ("CRRT") machine. While renal therapy is one focus of the present disclosure, the present disclosure also contemplates the integration of any home fluid delivery therapy, such as in addition, a home drug delivery therapy or a nutritional therapy. In various embodiments, the home therapy is any type of therapy using a medical fluid that can be made online, or at the time of use beginning with a source of purified water, such as ultrapure water as that term is understood in the art. For example, while PD has typically been performed using bagged dialysate, it is contemplated to instead make online PD solution beginning with the source of ultrapure or sterile water and adding PD concentrates, such as dextrose or glucose concentrate, as needed.

It is also contemplated that the home therapy is a nutritional therapy in which purified water from the water treatment device is used as the base for preparing a nutritional solution that is delivered to the patient. In any situation, all the control of the water treatment device is maintained through the same user interface that is used to control the home therapy machine, in one embodiment, be it a blood treatment home therapy machine, a PD home therapy machine or a nutritional home therapy machine.

It is contemplated for the home medical device system to transfer treatment prescriptions to the home therapy machine. A doctor's prescription for a renal or other type of home therapy is created. A clinician can remotely select, based upon the doctor's prescription, supplies to send to the patient's home, including supplies for both the home therapy machine and the water treatment device. The clinician can also remotely set operating parameters for operating both the home therapy machine and the water treatment device. The operating parameters for both the machine and device are sent to the home therapy machine. The operating parameters for the home therapy machine are stored in the memory of the therapy machine. The operating parameters for the water treatment device are forwarded from the home therapy machine to the water treatment device and stored in the memory of the water treatment device.

The system and method of the present disclosure also allow for the upgrading of firmware on the home therapy machine and the water treatment device via the home therapy machine. When upgraded firmware is generated, the firmware is sent to the home therapy machine. If the new firmware is meant for the home therapy machine, the new firmware is installed on the home therapy machine. If the new firmware is meant instead for the water treatment device, the home therapy machine forwards the new firmware to the water treatment device, where it is installed. In certain jurisdictions, it may be required that the user accept the software upgrade, be it for either the home therapy machine or the water treatment device. In either case, it is contemplated to allow the user to accept the new firmware, for either the machine or the device, at the user interface for the home therapy machine.

It is contemplated to provide operating prescriptions and new firmware with tags that designate which of the home therapy machine and the water treatment device is to receive the operating instructions or the firmware. Alternatively, the instructions and firmware may inherently look or have content that is peculiar to either the home therapy machine or the water treatment device. In this latter case, the home therapy machine can determine whether to itself accept the instructions or firmware upgrade or to forward same to the water treatment device based on the detected inherent characteristics. No additional tag is needed here.

Based on the foregoing and following description, it should be appreciated that it is an advantage of the present disclosure to provide an improved home therapy treatment using online purified water generation.

It is another advantage of the present disclosure to provide an improved hemodialysis, hemofiltration, hemodiafiltration, peritoneal dialysis, drug delivery, and nutritional home therapy system and method.

It is a further advantage of the present disclosure to provide an improved system and method for sending operating parameters to multiple machines or devices of a home therapy system.

It is yet another advantage of the present disclosure to provide clinicians, doctors and nurses with the ability to remotely review and monitor data produced by multiple machines or devices cooperating to provide a home therapy.

It is yet a further advantage of the present disclosure to provide an improved system and method for sending firmware upgrades to multiple machines or devices cooperating to provide a home therapy.

It is still another advantage of the present disclosure to ensure that data sent back and forth between a server and multiple machines or devices cooperating to provide a home therapy is performed in a reliable and secure manner.

It is still a further advantage of the present disclosure to prevent data from being delivered from a server to multiple machines or devices cooperating to perform a home therapy while the machines or devices are being operated.

Moreover, it is an advantage of the present disclosure to allow a user to control aspects of a treatment involving multiple machines or devices using one user interface.

Additional features and advantages are described herein and will be apparent from the following Detailed Description and the figures.

BRIEF DESCRIPTION OF THE FIGURES

FIG. 11A is a screen shot of an example treatment summary screen of the present disclosure.

FIG. 12 is a screen shot of an example patient usage report of the present disclosure.

DETAILED DESCRIPTION

Home Medical Device System

Figure 1A:
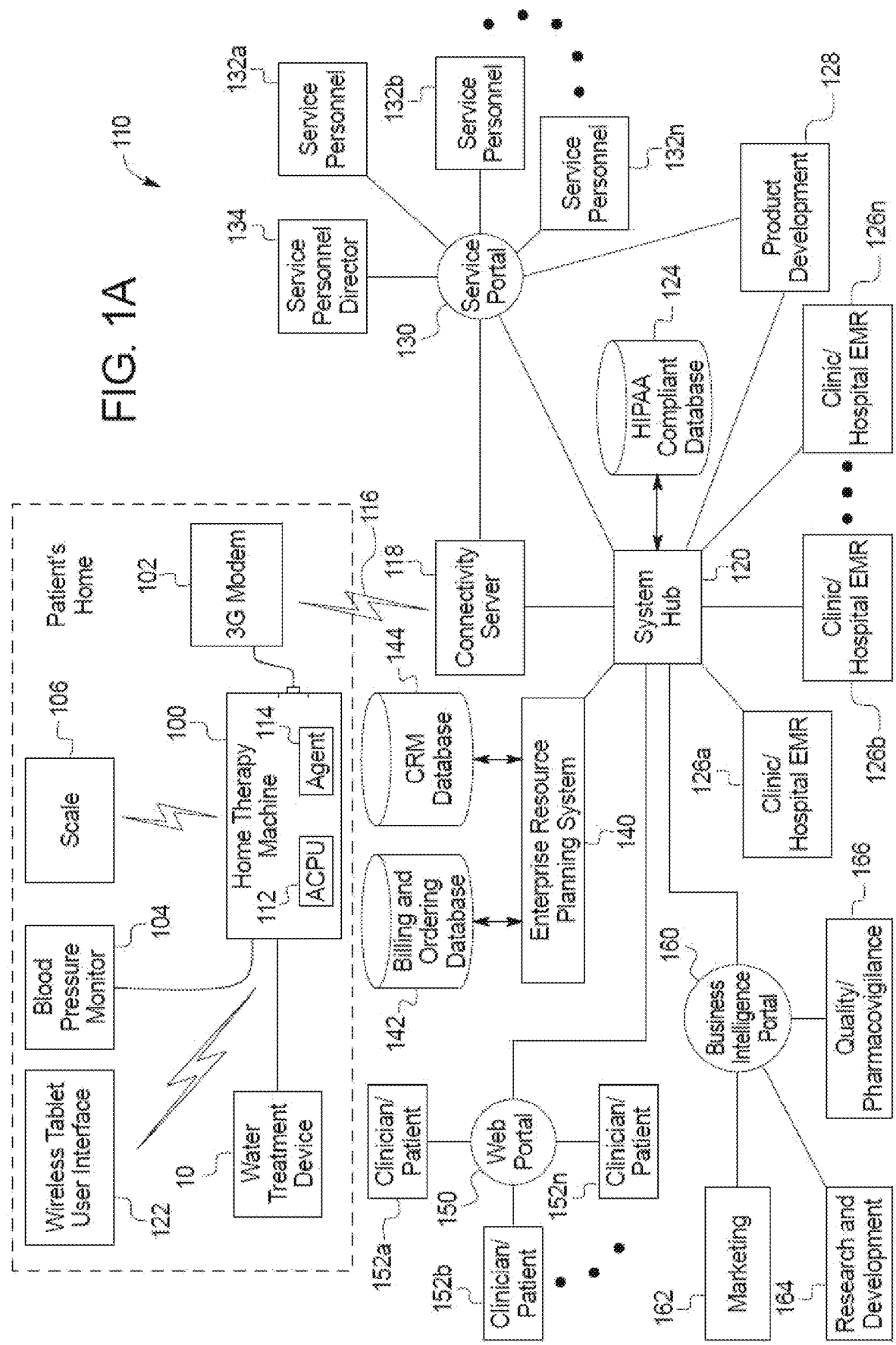
FIG. 1A is a schematic block diagram of one embodiment of a home medical device system of the present disclosure.

Referring now to the drawings and in particular to FIG. 1A, a home medical device system 110 is illustrated. System 110 shows a home therapy machine 100, which can be of any type including a home hemodialysis ("HD"), home hemofiltration ("HF"), home hemodiafiltration ("HDF"), home peritoneal dialysis ("PD"), home drug delivery, or nutritional home therapy machine. If home therapy machine 100 is a home hemodialysis machine, one suitable machine is set forth in U.S. Patent Publication No. 2009/0101549, entitled, "Modular Assembly For A Hemodialysis System", filed Aug. 27, 2008, the entire contents of which are incorporated herein by reference and relied upon.

While a single home therapy machine 100 is illustrated as communicating with a connectivity server 118, system 110 oversees the operation of a plurality of home therapy machines 100, of the same type or of different types. For example, there may be M number of hemodialysis machines 100, N number of hemofiltration machines 100, O number of hemodiafiltration machines 100, P number of peritoneal dialysis machines 100, Q number of home drug delivery machines 100, and R number of nutritional home therapy machines 100 connected to server 118 and operating with system 110. The numbers M through R may be the same or different numbers, and may be zero, one, or more than one.

In the illustrated embodiment, home therapy machine 100 receives at its front end purified water from a water treatment device 10. One suitable water treatment device 10 is set forth in U.S. Patent Publication No. 2011/0197971, entitled, "Water Purification System And Method", filed Apr. 25, 2011, the entire contents of which are incorporated herein by reference and relied upon. In one embodiment, water treatment device 10 outputs ultrapure water as that term is understood in the art. The ultrapure water may be passed through one or more filter, such as an ultrafilter or a dialyzer to make the water of or near an injectable or drug quality. The injectable quality water may then be mixed with one or more dry, liquid, or slurried concentrate to produce (i) an injectable substitution solution for HF or HDF, (ii) a PD solution, (iii) a drug for infusion or (iv) a nutritional solution for infusion.

System 110 illustrates that home therapy machines 100 operates with other devices besides water treatment device 10, such as a blood pressure monitor 104, a weigh scale, e.g., wireless weigh scale 106, and a wireless tablet user interface 122. Home therapy machine 100 connects to server 118 wirelessly in one embodiment via a modem 102. Each of these components, including water treatment device 10, are generally located within the patient's home, as demarcated by the dashed lines in FIG. 1A. Any one, or more or all of components 10, 104, 106 and 122 may communicate wired or wirelessly with home therapy machine 100. Wireless communication may be via Bluetooth™, WiFi™, Zigbee®, Z-Wave®, wireless Universal Serial Bus ("USB"), infrared, or any other suitable wireless communication technology. Alternatively, any one, or more or all of components 10, 104, 106 and 122 can communicate with home therapy machine 100 via wired communication.

In one embodiment, water treatment device 10 connects to home therapy machine 100 via an Ethernet cable. Water treatment device 10 is powered under its own power in one embodiment. Home therapy machine 100 can request water as needed from water treatment device 10. Water treatment device 10 is sized and configured to supply, on an online or batch basis, any amount of water that machine 100 needs.

Connectivity server 118 communicates with much of home medical device system 110 via a home medical device system hub 120. System hub 120 enables data and information concerning each home therapy machine 100 and water treatment device 10 on system 110 to travel back and forth via the connectivity server 118 between the machines 100 and the other clients connected to server 118. In the illustrated embodiment, system hub 120 is connected to a service portal 130, an enterprise resource planning system 140, a web portal 150, a business intelligence portal 160, a HIPAA compliant database 124, a product development team 128 and electronic medical records databases 126a to 126n.

The electronic medical records ("EMR") databases 126a to 126n contain electronic information about patients. The system hub 120 can send the data collected from log files of machine 100, described in detail below, to hospital or clinic databases 126a to 126n to merge or supplement that patient's medical records. Databases 126a to 126n may contain patient-specific treatment and prescription data and therefore access to such databases could be highly restricted. The enterprise resource planning system 140 obtains and compiles data generated via the patient and clinician website access, such as complaints, billing information and life cycle management information. Web portal 150 enables patients and clinics 152a to 152n treating the patients to access a publicly available website for system 110. Business intelligence portal 160 collects data from the system hub 120 and provides data to marketing 162, research and development 164, and quality/pharmacovigilance 166.

System Block Diagram

Figure 1B:
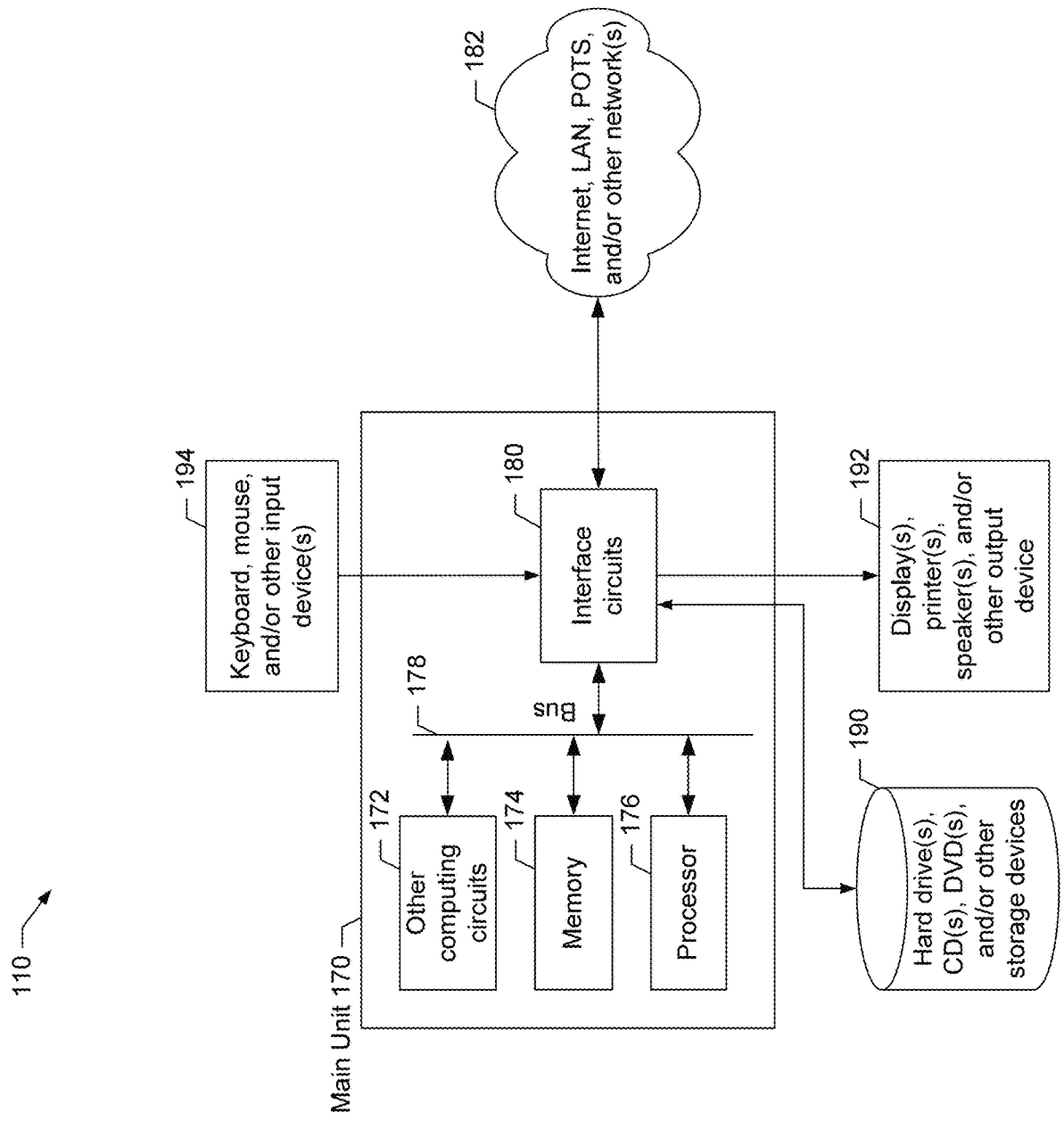
FIG. 1B is a block diagram of one embodiment of a computing device used in the home medical device system of the present disclosure.

A block diagram of one embodiment for the electrical systems of any or more or all of the machines, devices or subsystems of the home medical device system (e.g., water treatment device 10, machine 100, modem 102, blood pressure monitor 104, scale 106, server 118, system hub 120, user interface 122, service portal 130, enterprise resource planning system 140, web portal 150, business intelligence portal 160) is illustrated in FIG. 1B. System 110, including any or all of devices or subsystems 10, 100, 102, 104, 106, 118, 120, 122, 130, 140, 150, and 160, includes a main unit 170 which in one embodiment includes one or more processor 176 electrically coupled by an address/data bus 178 to one or more memory device 174, other computer circuitry 172, and one or more interface circuit 180. Processor 176 may be any suitable processor, such as a microprocessor from the INTEL PENTIUM® family of microprocessors. Memory 174 may include volatile memory and non-volatile memory. Memory 174 can store one or more software program that interacts with the other devices in the system 110 as described below. Memory 174 may also store digital data indicative of documents, files, programs, web pages, etc. retrieved from another computing device and/or loaded via an input device 194.

The interface circuit 180 may be implemented using any suitable interface standard, such as an Ethernet interface and/or a USB interface. One or more input device 194 may be connected to the interface circuit 180 for entering data and commands into the main unit 170. For example, input device 194 may be a keyboard, mouse, touch screen, track pad, track ball, isopoint, and/or a voice recognition system. Interface circuit 180 may be connected to any type of network 182, such as an Internet, a local area network ("LAN"), a telephone network (POTS), and/or other networks.

One or more displays, printers, speakers, and/or other output devices 192 may also be connected to the main unit 170 via the interface circuit 180. Display 192 may be a cathode ray tube (CRT's), liquid crystal displays (LCD's), or any other type of display. Display 192 generates visual displays of data generated during operation of the device or subsystem 10, 100, 102, 104, 106, 118, 120, 122, 130, 140, 150, and/or 160. For example, display 192 may be used to display information received from the system hub 120. The visual displays may include prompts for human input, run time statistics, calculated values, data, etc.

One or more storage device 190 may also be connected to the main unit 170 via the interface circuit 180. For example, a hard drive, CD drive, DVD drive, and/or other storage devices may be connected to the main unit 170.

It should be appreciated that the disclosed methods and procedures described herein may be implemented using one or more computer programs or components. These components may be provided as a series of computer instructions on any conventional computer-readable medium, including random access memory ("RAM"), read only memory ("ROM"), flash memory, magnetic or optical disks, optical memory, or other storage media. The instructions may be configured to be executed by a processor, which when executing the series of computer instructions performs or facilitates the performance of all or part of the disclosed methods and procedures.

Data Transfer for the Water Treatment Device

In one embodiment, home therapy machine 100 performs a home treatment, such as home hemodialysis on a patient at the patient's home and then reports the results of that treatment to clinicians, doctors and nurses who are responsible for managing the health and well-being of that patient. The results of the treatment include data that is supplied from water treatment device 10 to home therapy machine 100. Water treatment device 10 data can include, for example, total volume of water delivered, quality of water delivered (e.g., chlorine content), how many different times water treatment device 10 delivered water to therapy machine 100 over the course of a treatment (this data could be monitored by device 10 or machine 100), average flowrate of the water delivered, any alarms or alerts that water treatment device 10 experienced over a treatment, and/or an amount of time or number of cycles performed over the course of a treatment, e.g., for component replacement information.

Home therapy machine 100 writes log files using, e.g., a Linux™ operating system. The log files again document pertinent home therapy machine 100 data and pertinent water treatment device 10 data over the course of a treatment. The log files may include any one or more of Extensible Markup Language ("XML"), comma-separated values ("CSV") or text files. The log files are placed into a file server box of the software of home therapy machine 100. It is contemplated to store data at water treatment device 10 that is not sent to machine 100. Such data may otherwise be obtained via the Ethernet data connection to water treatment device 10 or downloaded through other data connections or storage media. For example, a service person can access additional data via a laptop connected to water treatment device 10 via the Ethernet connection. Or, the additional data may be retrieved remotely from water treatment device 10, with home therapy machine 100 serving as the data transfer liaison between water treatment device 10 and authorized system clients as described herein.

Home therapy machine 100, e.g., via the Internet, uses a connectivity service to transfer data, including water treatment device 10 data, between modem 102 and system hub 120. In one embodiment, a dedicated line is provided at each patient's home for connecting the home therapy machine 100 to the connectivity server 118 via modem 102. Home therapy machine 100 in one embodiment accesses the Internet using a separate, e.g., 3G, 4G or 5G, modem 102. Modem 102 uses an Internet Service Provider ("ISP"), such as Vodafone™. In one implementation, a connectivity agent 114 developed by a connectivity service provider (e.g., provider of connectivity server 118) is installed onto the home therapy machine 100 and run on primary control processor ("ACPU") 112. One suitable connectivity service is provided by Axeda™. The connectivity service provides a secure managed connection 116 between medical devices and the connectivity server 118.

The connectivity agent 114 allows the home therapy machine 100 to connect to connectivity server 118 and transfer data, including water treatment device 10 data, to and from the connectivity server 118. The connectivity service operating via agent 114 and server 118 ensures that the connection with machine 100 is secure, ensures that the data correctly passes through machine 100's firewalls, checks whether there has been a data or system crash and checks whether and ensures that the connectivity server 118 is communicating with the correct home therapy machine 100.

In one embodiment, home therapy machine 100 can only connect to the connectivity server 118 when connectivity agent 114 is turned on. During treatment and post-treatment disinfection, while machine 100 and water treatment device 10 are functioning, connectivity agent 114 is turned off. This prevents the home therapy machine 100 from communicating with any entity and sending or receiving data during treatment and disinfection or when machine 100 is live or running. When the home therapy machine 100 is idle, e.g., after treatment and post-disinfection is complete, ACPU 112 turns connectivity agent 114 on. In one embodiment, connectivity agent 114 is off only during treatment (including pretreatment). Connectivity agent 114 then retrieves the log files from the home therapy machine 100 and transfers data, including water treatment device 10 data, to the connectivity server 118 using the connectivity service. The connectivity service routes data packets to their proper destination but in one embodiment does not modify, access, or encrypt the data.

In system 110 of FIG. 1A, the connectivity service via connectivity server 118 can communicate data to various places via a system hub 120, a service portal 130 and a web portal 150. Connectivity server 118 allows service personnel 132a to 132n and/or clinicians to track and retrieve various assets across the network, such as appropriate home therapy machines 100 and 3G, 4G or 5G modem 102, and their associated information, including machine or modem serial numbers. The connectivity server 118 can also be used to receive and provide firmware upgrades, approved by a director of service personnel 134 and obtained remotely via service portal 130, to authorized home therapy machines 100 and their associated water treatment devices 10.

In one embodiment, a connectivity agent 114a (not illustrated) may also be installed on the water treatment device 10 in addition to being installed on the home therapy machine 100. If the home therapy machine 100 cannot communicate with the system hub 120, and system hub 120 needs to communicate with the water treatment device 10, the water treatment device 10 may then directly communicate with the system hub 120 via the connectivity agent 114a. Alternatively, connectivity agent 114a may be installed on a separate device or unit (not illustrated), which can be selectively connected to the water treatment device 10, so that water treatment device 10 can be converted so as to communicate directly with the system hub 120 again, for example, if home therapy machine 100 loses communication with system hub 120.

Servicing the Water Treatment Device

In one embodiment, home therapy machine 100 may be operated in a service mode for service personnel to access, diagnose and troubleshoot both home therapy machine 100 and water treatment device 10 on site and/or remotely. For example, if water treatment device 10 encounters a problem, or if a component of same, e.g., a chemical pack, becomes spent, the patient may be able to call a service personnel or technician. The patient and/or service person can then place water treatment device 10 via the home therapy machine 100 into a service mode that allows the service technician to remotely verify device 10 settings and functionality for various components of the water treatment device 10. In one embodiment, system 110 prevents treatment while the service technician is connected to machine 100 to enhance safety. For example, the service person may be able to logon onto device 10 via machine 100 while treatment is paused. Alternatively, machine 100 must be in an idle state, or even powered down, for the service person to be able to access the machine 100 and/or device 10. Further alternatively, the machine 100 need only be disconnected from the patient for the service person to be able to access the machine 100 and/or device 10.

Once accessed, the service technician can remotely investigate and retrieve the log files stored on the home therapy machine 100 for the water treatment device 10 to determine a cause of an error occurring on the water treatment device 10. The service person may also be able to toggle valves and actuate a pump, for example, to see if a related sensor, e.g., pressure sensor, of the water treatment device 10 is operating properly and/or if a valve or pump of the water treatment device 10 is operating properly. The service person does so by sending a command to home therapy machine 100. Home therapy machine 100 recognizes that the command is for water treatment device 10 and passes along the command to the processing and memory of the water treatment device 10, which in turn causes the appropriate action to occur on water treatment device 10. Water treatment device 10 sends response data back to home therapy machine 100, which relays the information back to the appropriate service person.

Requests sent from the service person can either be structured so that machine 100 inherently knows whether the request is for home therapy machine 100 or water treatment device 10. Alternatively, the request can be tagged. For example, the valves for home therapy machine 100 may be numbered consecutively starting from the number one, while the valves for water treatment device 10 may be numbered consecutively starting from the number one-hundred (assuming home therapy machine 100 has less than one-hundred valves). Here, it is inherently known to pass a request to toggle valve one-hundred-eleven along to water treatment device 10. Alternatively, the valves for both home therapy machine 100 and water treatment device 10 may be numbered consecutively starting from the number one, but wherein the requests are coded, e.g., "A" for home therapy machine 100 and "B" for water treatment device 10. Here, ACPU 112 of home therapy machine 100 knows to keep a request to toggle valve AV4 and to pass along a request to toggle valve BV4 to water treatment device 10.

Control Via One User Interface

In one embodiment, the control processor (ACPU 112) and user interface 122 of home therapy machine 100 walk the patient through the entire treatment process and instruct, on a step-by-step basis, as to how treatment should be initiated and performed, including instructions for operating water treatment device 10. In one embodiment, the user interface 122 is a tablet that runs a custom, secure interface that only allows access to the home therapy machine 100. In one implementation, tablet 122 operates wirelessly. Tablet 122 here can plug into home therapy machine 100 initially for pairing the tablet 122 with the home therapy machine 100 and for performing software (e.g., firmware) upgrades for the tablet 122. Tablet 122 may also plug into home therapy machine 100 to power or charge the tablet 122. Connectivity between tablet 122 and home therapy machine 100 may be via a serial data connection, over a universal serial bus ("USB") connection, parallel connection or via another suitable data transfer interface. Once the tablet 122 is paired to the home therapy machine 100, the tablet 122 communicates wirelessly (e.g., using Bluetooth™ or WiFi™) with the home therapy machine 100.

Figure 3:
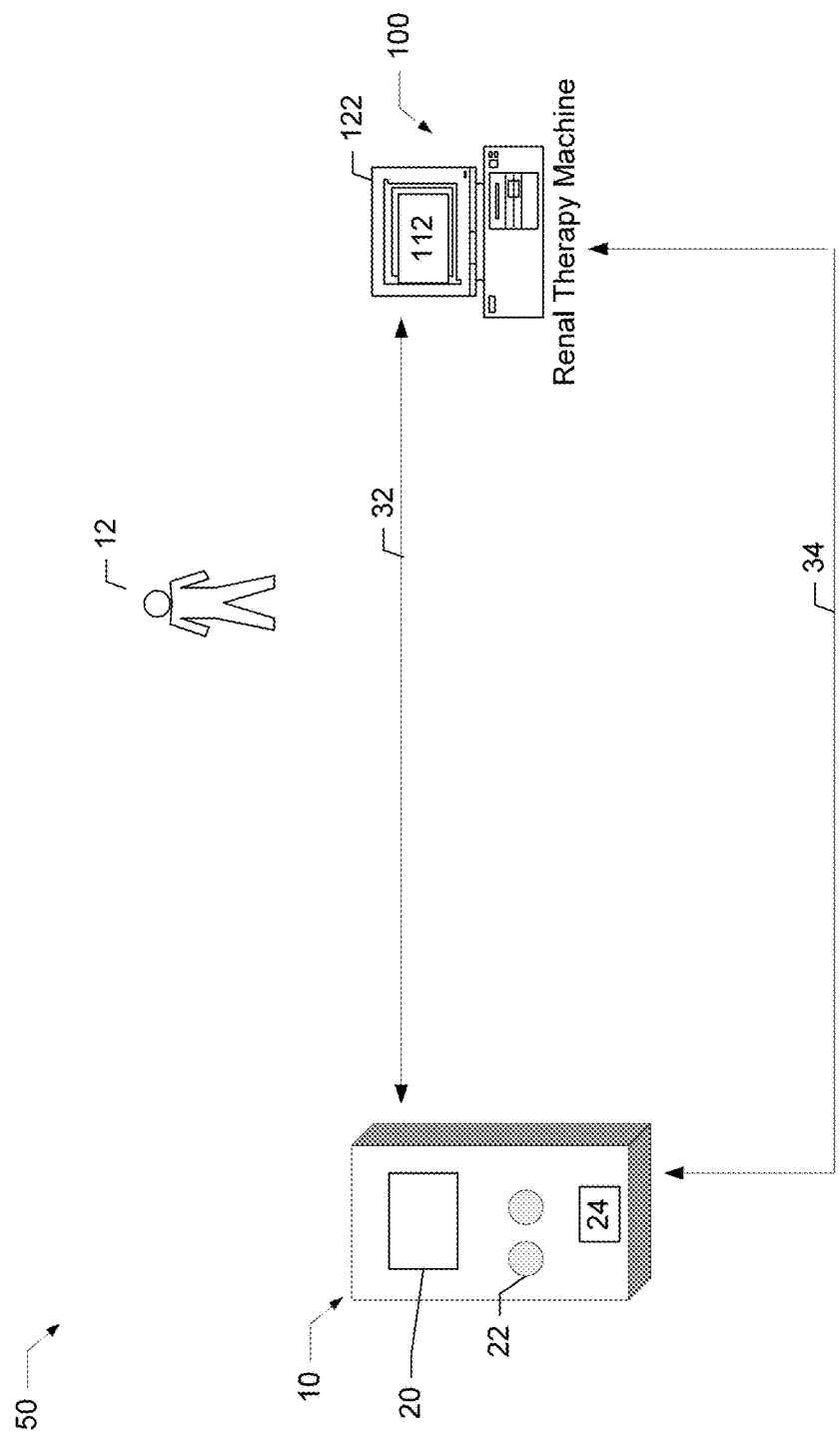
FIG. 3 is a schematic view of one embodiment of a subsystem including a water treatment device in communication with a home therapy machine for a home medical device system of the present disclosure.

User interface 122 can alternatively be connected to or tethered to machine 100, for example, as shown and described in U.S. Patent Publication No. 2009/0114582, the entire contents of which are incorporated herein by reference and relied upon. A connected or tethered arrangement for user interface 122 is accordingly discussed below, as illustrated in FIG. 3.

In one embodiment, the user can send data to and receive data from machine 100 via tablet 122. Data entered into the user interface 122 is securely sent to the home therapy machine 100 and processed in ACPU 112, which controls machine 100 or forwards commands to be processed by water treatment device 10, which in turn controls some operation of the water treatment device 10. In one embodiment, no treatment data is stored in tablet 122. Storing no treatment data in the tablet 122 is advantageous because if the tablet 122 is disconnected or lost, no sensitive or important data is lost.

Because user interface 122 of home therapy machine 100 is also used to enter and display data related to water treatment device 10, water treatment device 10 does not need and in one embodiment does not provide anything more than a simple display, which may be provided with a few electromechanical buttons, such as membrane switches, and an on/off switch. The simple display may be a small liquid crystal display ("LCD") or light emitting diode ("LED") display, which provides a single line or few lines of text. The electromechanical buttons allow for emergency control of water treatment device 10 in case tablet 122 is lost or communication between home therapy machine 100 and water treatment device 10 is broken. The electromechanical buttons alternatively or additionally allow installation or service of the water treatment device 10 in the absence of the home therapy machine 100. The electromechanical buttons may also allow a service person to enter a service mode directly from the small keypad, e.g., by pressing and holding a hidden button for a certain number of seconds.

In one embodiment, the user may power and depower home therapy machine 100 and/or water treatment device 10 from common user interface 122. A user may send a command to water treatment device 10 from common user interface 122. The command may for example request that water treatment device 10 provide an estimate of how much time exists before a consumable component of water treatment device 10 needs replacement. For example, water treatment device 10 may include a carbon filter, a sediment removal cartridge, softening filter, reverse osmosis ("RO") membrane or metallic catalyst filter, which each needs to be replaced after a certain number of hours of use. Like before, the command from tablet 122 may be inherent to water treatment device 10, so that ACPU 112 has no choice but to forward the command to water treatment device 10. Or, the command may be provided with a code that ACPU 112 recognizes, upon which ACPU 112 responsively forwards the command to water treatment device 10.

One goal of the present disclosure is to prevent the user from having to look at two different user interfaces when performing the home therapy treatment under system 110. Besides allowing user interface 122 to be a common user interface, it is contemplated to make water treatment device 10 require as little user interaction as possible. For example, water treatment device 10 can be configured such that it remains powered indefinitely with no ill affect to the water treatment device 10. Or, home therapy machine 100 and water treatment device 10 can be configured such that water treatment device 10 receives power whenever home therapy machine 100 is powered. In a similar manner, many commands to home therapy machine 100 may carry over or have an automatic secondary affect on water treatment device 10. For example, a PAUSE or STOP input from user interface 122 to home therapy machine 100 may likewise cause home therapy machine 100 to automatically issue a PAUSE or STOP command to water treatment device 10. In another example, if home therapy machine 100 enters an alarm state while receiving purified water from water treatment device 10, home therapy machine 100 can cease pumping water from water treatment machine 10.

Operating parameters for home therapy machine 100 may also dictate operating parameters for water treatment device 10. For example, in the hemodialysis realm, dialysis fluid or dialysate flowrate entered as an operating parameter into home therapy machine 100 can dictate the flowrate at which water treatment device 10 is commanded to produce purified water, which is used to make the dialysis fluid or dialysate. This leader/follower operating parameter arrangement can be carried out in a plurality of different ways. In one way, ACPU 112 of home therapy machine 100 calculates or finds via a look-up table the operating parameter for water treatment device 10 based on the corresponding operating parameter for home therapy machine 100. For example, ACPU 112 may store that purified water flowrate is to be set to 1.2 times the dialysate flowrate. ACPU 112 calculates and adjusts on the fly a purified water flowrate knowing the current actual or currently commanded flowrate of dialysate for home therapy machine 100. In one embodiment, ACPU 112 may adjust the purified water flowrate if ACPU 112 determines that the patient needs a bolus of fresh solution. One suitable method for providing the patient with a bolus of fresh solution is set forth in U.S. Patent Publication No. 2009/0124963, entitled, "Balanced Flow Dialysis Machine", filed Nov. 9, 2007, the entire contents of which are incorporated herein by reference and relied upon.

In a second way, the control processor of water treatment device 10 calculates or finds via a look-up table the operating parameter for water treatment device 10 based upon the corresponding operating parameter for home therapy machine 100 sent by the home therapy machine 100 to the water treatment device 10. For example, the control processor of water treatment device 10 may store that purified water flowrate is to be set to 1.2 times the dialysate flowrate. ACPU 112 sends current dialysate flowrate periodically to water treatment device 10, which in turn calculates and adjusts on the fly a purified water flowrate knowing the current actual or currently commanded flowrate of dialysate for home therapy machine 100.

In a third way, the control processor of water treatment device 10 runs off of a prescription just like home therapy machine 100. Discussed below is a process by which home therapy machine 100 receives one or more machine operating prescriptions from a doctor or clinician remotely via the server 118 and system hub 120 discussed above. When a machine operating prescription is installed onto ACPU 112 of home therapy machine 100, the prescription comes with a set of instructions or secondary prescription that is forwarded from ACPU 112 to the control processor of water treatment device 10. When that prescription for the home therapy machine 100 is then recalled by the user for treatment via home therapy machine 100, the corresponding set of instructions or secondary prescription is recalled for use with water treatment device 10. In this third way, updating data during treatment between home therapy machine 100 and water treatment device 10 can be reduced or eliminated.

A fourth way works on a batch or volume basis. Home therapy machine 100 can include a dialysate holding tank. ACPU 112 can be configured to make dialysate when tank volume falls to a certain level and stop making dialysate when tank volume rises to a certain level. Here, water treatment device 10 is tasked with providing enough water to raise the low dialysate tank volume to the high dialysate tank volume as opposed to being concerned with dialysate flowrate to the dialyzer. When tank volume hits the low level, ACPU 112 activates water treatment device 10 and the dialysate mixing pumps of home therapy machine 100 to produce dialysate and attempt to fill the dialysate holding tank. Water treatment device 10 and the dialysate mixing pumps remain activated until the designated high tank volume is reached. It is contemplated to maintain different dialysate production rates for water treatment device 10 and the dialysate mixing pumps, so that if the water treatment device 10 and the dialysate mixing pumps cannot meet demand at a lower rate of production, they can be raised to a higher rate of dialysate production. As ACPU 112 raises or lowers the dialysate production rate, the water treatment device 10 and the dialysate mixing pumps are both adjusted accordingly.

While dialysate flowrate/purified water flowrate and/or volume control has been used to illustrate the leader/follower operating parameter arrangements, it is expressly contemplated to use the arrangements with other parameters, such as parameters relating to the pressure, temperature and/or purity level of the water exiting water treatment device 10.

Figure 2:
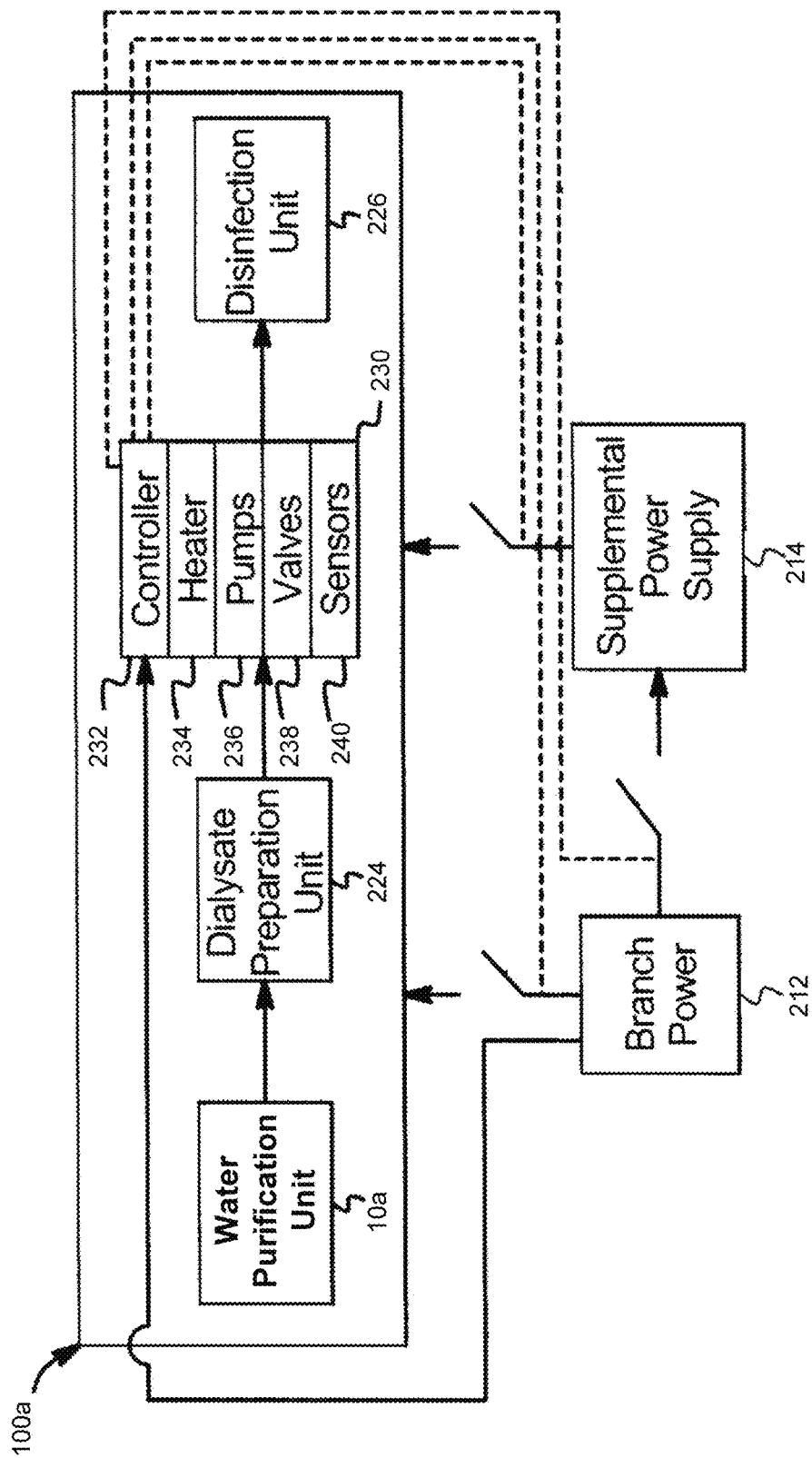
FIG. 2 is a block diagram of one embodiment of a dialysis machine with a water purification unit in a home medical device system of the present disclosure.

Referring now to FIG. 2, an example dialysis machine 100*a* includes a water purification unit 10*a*, a dialysate preparation unit 224, a dialysate delivery unit 230 and a disinfection unit 226. Controller 232 in one embodiment includes a plurality of controllers, each including processing and memory. Controller 232 can for example include a master or supervisory processor that controls a plurality of delegate processors, each of which are dedicated to various functions related to dialysis machine 100*a*. Controller 232 can also include redundant processing, such as a safety processor which ensures that each of the other processors is performing its function correctly.

Controller 232 can control any one or more of water purification unit 10*a*, dialysate preparation unit 224 and disinfection unit 226 in addition to controlling heater 234, pumps 236, valves 238 and sensors 240. Home therapy machine and water treatment device are shown as being separate in FIG. 1A, but they may be in the same housing as shown in FIG. 2. In one embodiment, the same user interface 122 may be used to control the controller 232, which may control any one or more of the various units, e.g., home therapy machine as well as water treatment device. The dialysis machine 100*a* may be powered by branch power 212 and/or supplemental power supply 214.

Data Connection

Referring now to FIG. 3, FIG. 3 illustrates a subsystem 50 of system 110 between water treatment device 10 and home therapy machine 100. For reference, the simple display and electromechanical buttons discussed previously for water treatment device 10 are illustrated by display 20 and electromechanical buttons 22. Alternatively, water treatment device 10 only includes display 20 and provides only rudimentary input devices. The display on the water treatment device 10 may augment the user interface 122. The control processing and memory for water treatment device 10 is illustrated by processing and memory 24. Also, as mentioned above, user interface 122 of home therapy machine 100 is illustrated as being tethered or connected to the home therapy machine 100. User interface 122 is alternatively an untethered tablet as has been described herein.

As illustrated in FIG. 3, a data communication link 32, e.g., Ethernet or wired communication, is provided to transmit data between processing and memory 24 of water treatment device 10 and ACPU 112 of home therapy machine 100. In one example, water treatment device 10 uses link 32 to send to the home therapy machine 100 state or status information, component life information, sensor levels or readouts, self test results, alert and alarm information and hardware and/or software version information. The water treatment device 10 can also indicate information about the water flow between the water treatment device 10 and the home therapy machine 100 including flowrate information, water temperature information and line connection disinfection information.

As further illustrated in FIG. 3, data communication link 32 may also be used to transmit data between ACPU 112 of home therapy machine 100 and processing and memory 24 of water treatment device 10. As discussed above, or in addition to above, home therapy machine 100 can send to the water treatment device 10 data regarding state change requests, commands (e.g., RUN, PAUSE or STOP), status queries, flowrate change requests, software upgrades or downgrades, and/or file, e.g., device prescription, transfers.

As discussed herein, user interface 122 indicates information about the water treatment device 10 to user 12. For example, the user interface 122 may display to user 12 information such as an alarm or an alert notice, water treatment device performance information, trouble shooting help, task guidance and/or action requests. For example, user 12 via user interface 122 can ask water treatment device 10 to identify itself to ensure data connection 32 between machine 100 and device 10 is functioning properly and to verify compatibility, such as hardware version and software version compatibility, between device 10 and machine 100. If so, device 10 can itself make an audible beep or answer and/or send a confirming message back to user interface 122, e.g., "I am here". The user 12 can then take appropriate action, either via user interface 122 or by performing some task indicated by the user interface 122. To do so, user 12 need only interact with common user interface 122. In this way, user 12 can have minimal interaction with water treatment device 10, such as to perform a hard power-on and off, make physical data and power connections, perform filter changes and/or take manual measurements, while ensuring that water treatment device 10 is functioning properly and in communication with machine 100.

In addition to the data connection 32 between home therapy machine 100 and water treatment device 10, there is a water feed line 34 running from water treatment device 10 to home therapy machine 100. Water feed line 34 sends water at a specified level of sterility, flowrate, pressure and/or temperature to home therapy machine 100. Water sent from the water treatment device 10 to the home therapy machine 100 is maintained typically at between about 5° C. and 35° C. Line 34 may in one embodiment be used to return unused water product from home therapy machine 100 to water treatment device 10.

In one embodiment, processing and memory 24 of water treatment device 10 operate as a slave or delegate processor to the programmed ACPU 112 of home therapy machine 100. The water treatment device 10 can inform the home therapy machine 100 of its status, such as an alarm situation, and send any other pertinent data to ACPU 112. Home therapy machine 100 stores and acts upon the data, e.g., decides whether to raise an alarm. Home therapy machine 100 thus controls the behavior of water treatment device 10.

Water treatment device 10 may be in any one of several different states, such as "Installation", "System Rinse", "Hibernate" or "Therapy". Home therapy machine 100 is responsible in one embodiment for requesting that water treatment device 10 changes states, e.g., from "Hibernate" to "Therapy". In "Hibernate", water treatment device 10 is maintained in a minimum power usage state. In "Therapy", water treatment device 10 is brought to a fully capable power level. As discussed above, the present system and method contemplate many ways of pairing water treatment device 10 to home therapy machine 100 upon a request for water by the home therapy machine 100. In each alternative, water treatment device 10 provides water suitable for treatment, and in a suitable quantity or flowrate, to home therapy machine 100.

Water treatment device 10 may send information to be displayed on the user interface 122 to prompt necessary user actions. Water treatment device 10 may send status information to the home therapy machine 100 asynchronously or in response to a status query. The water treatment device 10 may also send error packets to the home therapy machine 100 in case of an error or an alarm. The home therapy machine 100 can decide what actions need to be taken and whether the user 12 should be notified via user interface 122. If the user 12 needs to provide any input for clearing the alarm, the user 12 can do so via user interface 122. Water treatment device 10 is responsible for notifying home therapy machine 100 about its current state. Water treatment device 10 is also responsible for notifying home therapy machine 100 about any alarms or alerts.

When water is required for therapy, home therapy machine 100 in one embodiment discussed above specifies to the water treatment device 10 the desired flowrate of the water. The water treatment device 10 then provides water at the desired flowrate. Or, as discussed above, water treatment device 10 calculates or looks up its flowrate based upon a therapy fluid flowrate sent from home therapy machine 100. Or, as discussed above, water treatment device 10 determines its flowrate from its own device prescription. Still further as provided above, water treatment device 10 and home therapy machine 100 can instead cooperate on a volumetric basis.

It should be appreciated that using and controlling both water treatment device 10 and home therapy machine 100 from the user interface 122 increases safety, minimizes the complexity of operating multiple devices and reduces the burden of therapy on patients at home. The functioning of water treatment device 10 and the home therapy machine 100 is also streamlined via the master/delegate processor arrangement.

Installing Water Treatment Device

Figure 4:
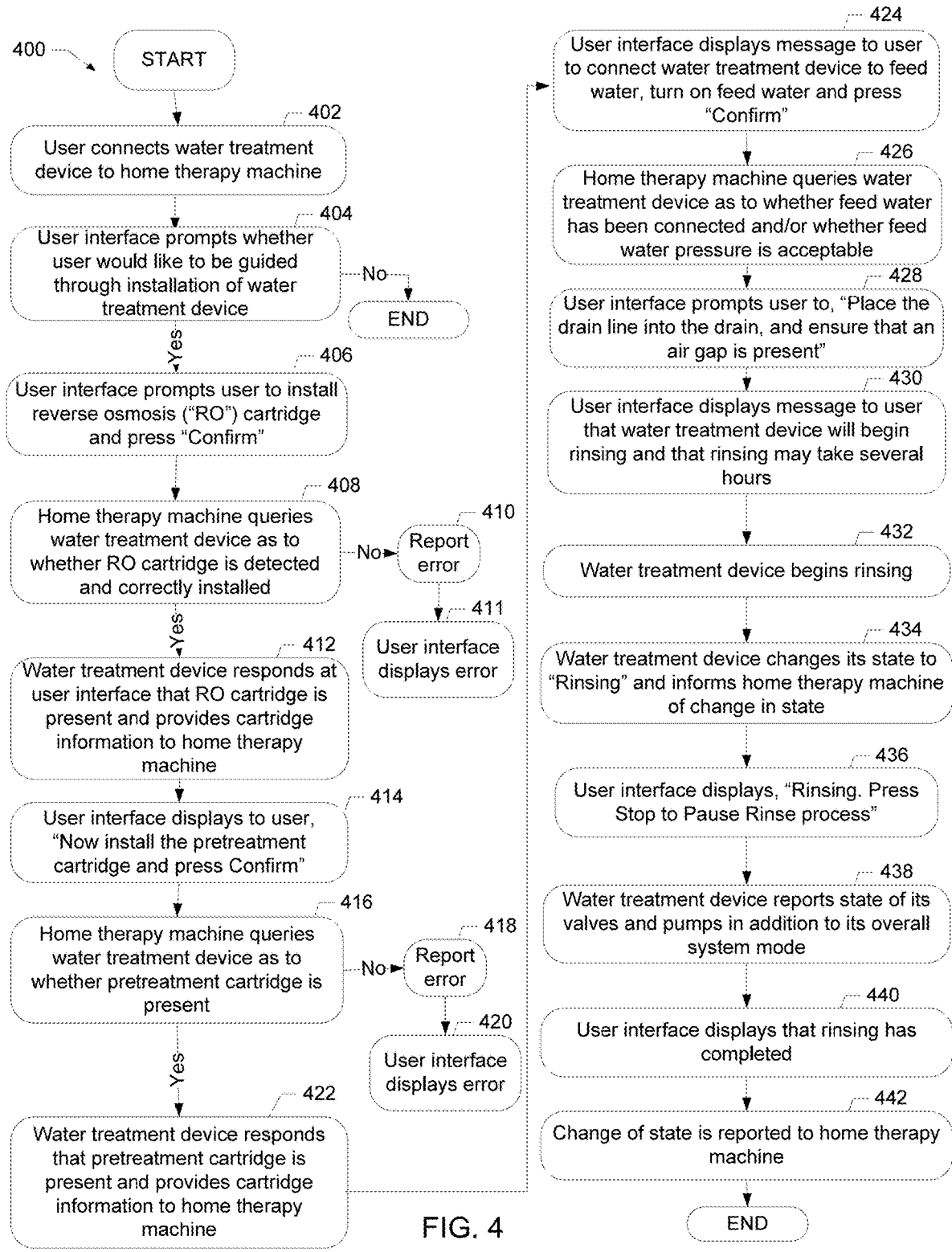
FIG. 4 is a flowchart of an example process of the present disclosure for installing a water treatment device.

It is contemplated under system 110 for water treatment device 10 and home therapy machine 100 to work together in many different ways, facilitated in many instances by common user interface 122. Referring now to FIG. 4, for example, process 400 illustrates an example process for installing or initially setting up water treatment device 10 using user interface 122 of home therapy machine 100. Upon starting process 400 at the start oval, a user 12 connects water treatment device 10 to the home therapy machine 100 as shown at block 402, e.g., makes data connection 32 and water line connection 34 discussed above. User interface 122 upon sensing the data connection prompts the user 12 whether the user would like to be guided through installation of the water treatment device 10, as shown at block 404. If the user 12 selects "No", process ends at the end oval near block 404. If the user 12 selects "Yes", user interface 122 prompts the user 12 to first install an RO cartridge and press "Confirm" on user interface 122, as shown at block 406.

When the user 12 presses "Confirm", home therapy machine 100 queries water treatment device 10 as to whether the RO cartridge is detected and correctly installed, as shown at block 408. If the RO cartridge is not detected or not correctly installed, water treatment device 10 reports an error condition as shown at block 410, and displays an error message on user interface 122, as shown at block 411. If the RO cartridge is detected and correctly installed, water treatment device 10 responds at user interface 122 that the RO cartridge is present and provides cartridge information to the home therapy machine 100, as shown at block 412.

Next, user interface 122 displays to the user 12, "Now install the pretreatment cartridge and press Confirm", as shown at block 414. When the user 12 installs the cartridge and presses "Confirm" at user interface 122, home therapy machine 100 queries the water treatment device 10 as to whether the pretreatment cartridge is present, as shown at block 416. If the pretreatment cartridge is not present or there is an error, the water treatment device 10 responds with a pretreatment cartridge error, as shown at block 418, in which case the user interface 122 displays a message to the user 12 that the pretreatment cartridge is not installed properly, as shown at block 420. If the pretreatment cartridge is present, the water treatment device 10 responds that the pretreatment cartridge is present and provides cartridge information to the home therapy machine 100, as shown at block 422.

Next, user interface 122 displays a message to the user 12 to connect the water treatment device 10 to feed water, turn on the feed water and press "Confirm", as shown at block 424. When the user 12 presses "Confirm", home therapy machine 100 queries water treatment device 10 as to whether the feed water has been connected and/or whether the feed water pressure is acceptable, as shown at block 426.

Next, user interface 122 prompts the user 12 to, "Place the drain line into the drain, and ensure that an air gap is present", as shown at block 428. Once the user 12 confirms these steps, user interface 122 displays a message to the user 12 that the water treatment device 10 will begin rinsing and that rinsing may take several hours, as shown at block 430. The user interface 122 also displays a "Rinse" button. Once the user 12 presses the displayed "Rinse" button, water treatment device 10 begins rinsing, as shown at block 432. A separate "Rinse" button accordingly need not be provided on water treatment device 10, although one may be provided for redundancy. In any case, water treatment device 10 changes its state to "Rinsing" and informs home therapy machine 100 of this change in state, as shown at block 434. User interface 122 displays, "Rinsing. Press Stop to Pause Rinse process", and displays a "Stop" or "Pause" button accordingly, as shown at block 436. Water treatment device 10 may also report the state of its valves and pumps in addition to its overall system mode, as shown at block 438. When the rinsing is complete, user interface 122 displays that rinsing has been completed, as shown at block 440. A change of state is also reported to home therapy machine 100, as shown at block 442. Process 400 then ends as illustrated at the end oval.

It should be appreciated that while the steps of process 400 involve specific functions to be performed on water treatment device 10, the display of instructions and user inputs for same occur on the user interface 122. Thus, the user 12 can focus solely on user interface 122 to install the water treatment device 10 and to run treatment on home therapy machine 100.

Making Water

Figure 5:
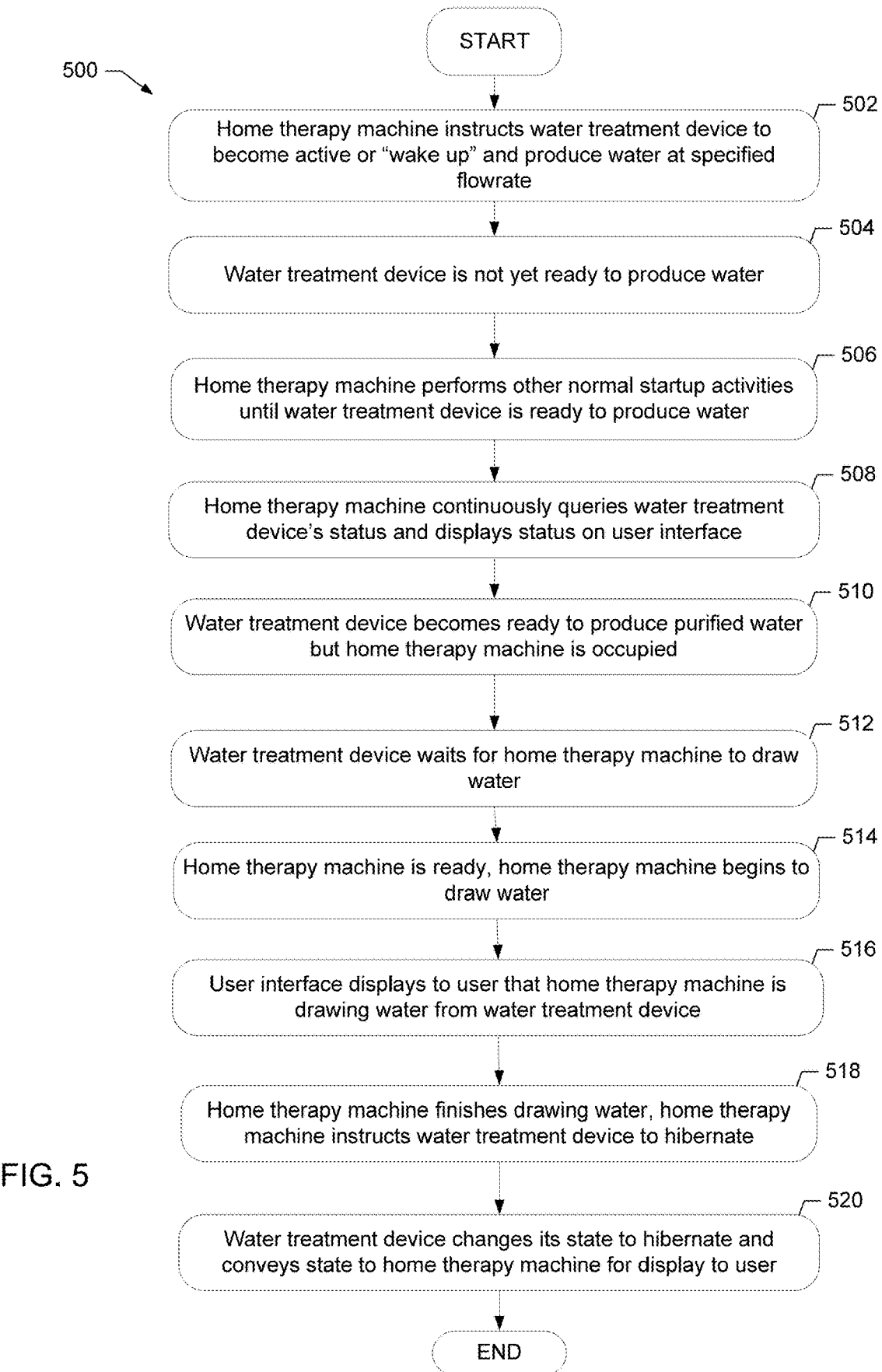
FIG. 5 is a flowchart of an example process of the present disclosure for making water with a water treatment device.

FIG. 5 illustrates an example process 500 for making water with water treatment device 10 using user interface 122 of home therapy machine 100. Upon starting process 500 at the start oval, home therapy machine 100 instructs water treatment device 10 to become active or "wake up" and produce water at a specified flowrate (or until a specified volume of dialysate is reached in the dialysate holding tank), as shown at block 502. In one embodiment, the water treatment device 10 performs necessary functions prior to producing water. Upon becoming active or waking up, home therapy machine 100 performs startup activities, such as self-tests, rinsing, and safety checks. When water treatment device 10 has completed the activities required, the device "wakes-up" and is ready to produce water, as shown at block 506. Home therapy machine 100 continuously queries water treatment device 10's status and displays such status on user interface 122, as shown at block 508. When water treatment device 10 is finished waking up and is ready to produce purified water, if home therapy machine 100 is occupied, as shown at block 510, water treatment device 10 waits for the home therapy machine 100 to draw water, as shown at block 512. Once home therapy machine 100 is ready, home therapy machine 100 begins to draw water, as shown at block 514. User interface 122 displays to the user 12 that the home therapy machine 100 is drawing water from water treatment device 10, as shown at block 516.

User interface 122 may also provide an option for the user 12 to change the water preparation flowrate of water treatment device 10 or to pause or stop production of same. Or as discussed above, home therapy machine 100 may instruct water treatment device 10 to change the flowrate based upon instructions stored in the ACPU 112. Water treatment device 10 in one embodiment is configured to change its recovery ratio based on demand. The RO units of water treatment device 10 produce reject water. The reject water can be reclaimed and fed back into the RO units, reducing water actually rejected to drain, but doing so can reduce the service life of the RO units because feeding the RO units with recycled reject water can cause fouling to occur. However, in the event that home therapy machine 100 is not using all of the available stream of purified water produced by water treatment device 10, the rejected water stream from the RO units can be mixed with the excess purified water, creating a solution that is functionally equivalent to tap water, and which will not cause excessive fouling of the RO units. In this way, the water treatment device 10 can adjust the amount of rejected RO water to be recycled based upon the availability of unused purified water that can be mixed with the reject stream prior to reentering the RO units.

When home therapy machine 100 is finished drawing water, home therapy machine 100 instructs water treatment device 10 to hibernate, as shown at block 518. In hibernate, water treatment device 10 continues to communicate with home therapy machine 100 to wait for an eventual command to wake-up again. Also, in hibernate water treatment device 10 may periodically perform rinses of its flow path after set periods of stagnation to maintain its performance in the absence of a command to wake-up. Water treatment device 10 changes its state to hibernate and conveys its state to the home therapy machine 100 for display to user 12, as shown at block 520. Process 500 then ends as illustrated at the end oval.

Starting Up Home Therapy Machine and Water Treatment Device

Figure 6:
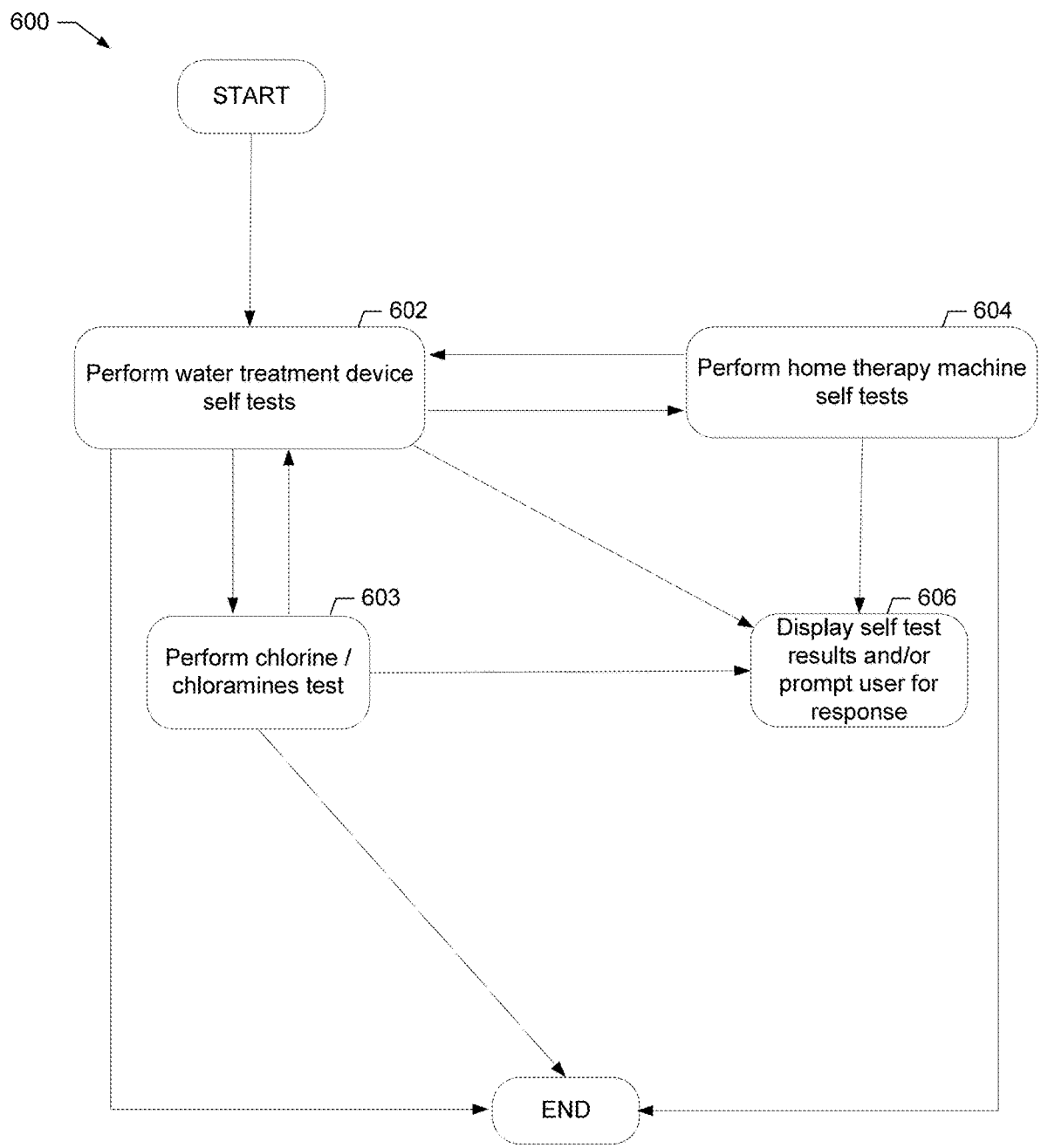
FIG. 6 is a flowchart of an example process of the present disclosure for starting up a home therapy machine and a water treatment device.

FIG. 6 illustrates an example process 600 for starting up home therapy machine 100 and water treatment device 10 using user interface 122 of home therapy machine 100. Upon starting process 600 at the start oval, user interface 122 walks the user 12 through start-up tests related to water treatment device 10, as shown at block 602. For example, user interface 122 can ask the user 12 to check and run self tests for the UV light intensity, RO rejection percentage and total organic carbon ("TOC") level, each associated with water treatment device 10. Other self tests associated with water treatment device 10 include, for example, whether or not remaining pretreatment cartridge life is sufficient.

The water treatment device 10 self tests may include a chlorine/chloramines test. For example, the ACPU 112 may decide that a chlorine/chloramines test should be run. The user interface 122 may prompt the user to collect a water sample from water treatment device 10 for testing, optionally by pressing a button on user interface 122. A chlorine/chloramines test is performed, as shown at block 603, and the user interface 122 displays to the user chlorine/chloramines test result options (e.g. Pass or Fail) and may prompt the user for a response, as shown at block 606. Depending upon the result of the chlorine/chloramines test, process 600 may either complete other self testing for device 10, return to home therapy machine 100 self testing or proceed with a different task for the water treatment device 10.

Process 600 may accordingly interleave between steps 602 and 603 as shown by the dual direction arrows between steps 602 and 603. For example, if the water treatment device 10 does not pass the chlorine/chloramines test, home therapy machine 100 may signal to the water treatment device 10 that a pretreatment swap is required or that the sample needs to be retested to confirm a failure. The water treatment device 10 changes its system state to "Cartridge Swap" and confirms the state change to ACPU 112. User interface 122 displays to user 12 that water treatment device 10 requires a pretreatment cartridge swap. The user interface 122 then walks user 12 through the steps for swapping the pretreatment cartridge. Any errors from the water treatment device 10 are displayed to the user 12 via user interface 122, or user interface 122 may prompt the user for a response, as shown at block 606. Upon completion of the steps for the pretreatment cartridge swap, the water treatment device 10 changes its state and conveys its state to the home therapy machine 100 for display to user 12.

If all the self tests associated with water treatment device 10 have positive results with no errors, user interface 122 transitions to running self tests for home therapy machine 100, as shown at block 604. Or, ACPU 112 may alternate self tests between home therapy machine 100 and water treatment device 10. In other words, it may not be desirable to run all of the home therapy machine 100 self tests first and then run the water treatment device 10 self tests, or vice versa, as discussed above. The self tests may be interleaved or run simultaneously. Process 600 may accordingly interleave between steps 602, 603 and 604 as shown by the dual direction arrows between steps 602 and 603 and 602 and 604. At any time, the self test for either home therapy machine 100 or water treatment device 10 may display a result to or prompt user 12 for a response on user interface 122, as shown at block 606. Such interleaving of testing increases efficiency and saves time, while enabling the user 12 to pay attention to a single user interface 122.

Process 600 ends as illustrated at the end oval, and may end from any one of steps 602, 603 or 604, depending upon the results of the self tests and the order of interleaving between the self tests.

Performing Pre-Treatment Cartridge/Membrane Swap

Figure 7:
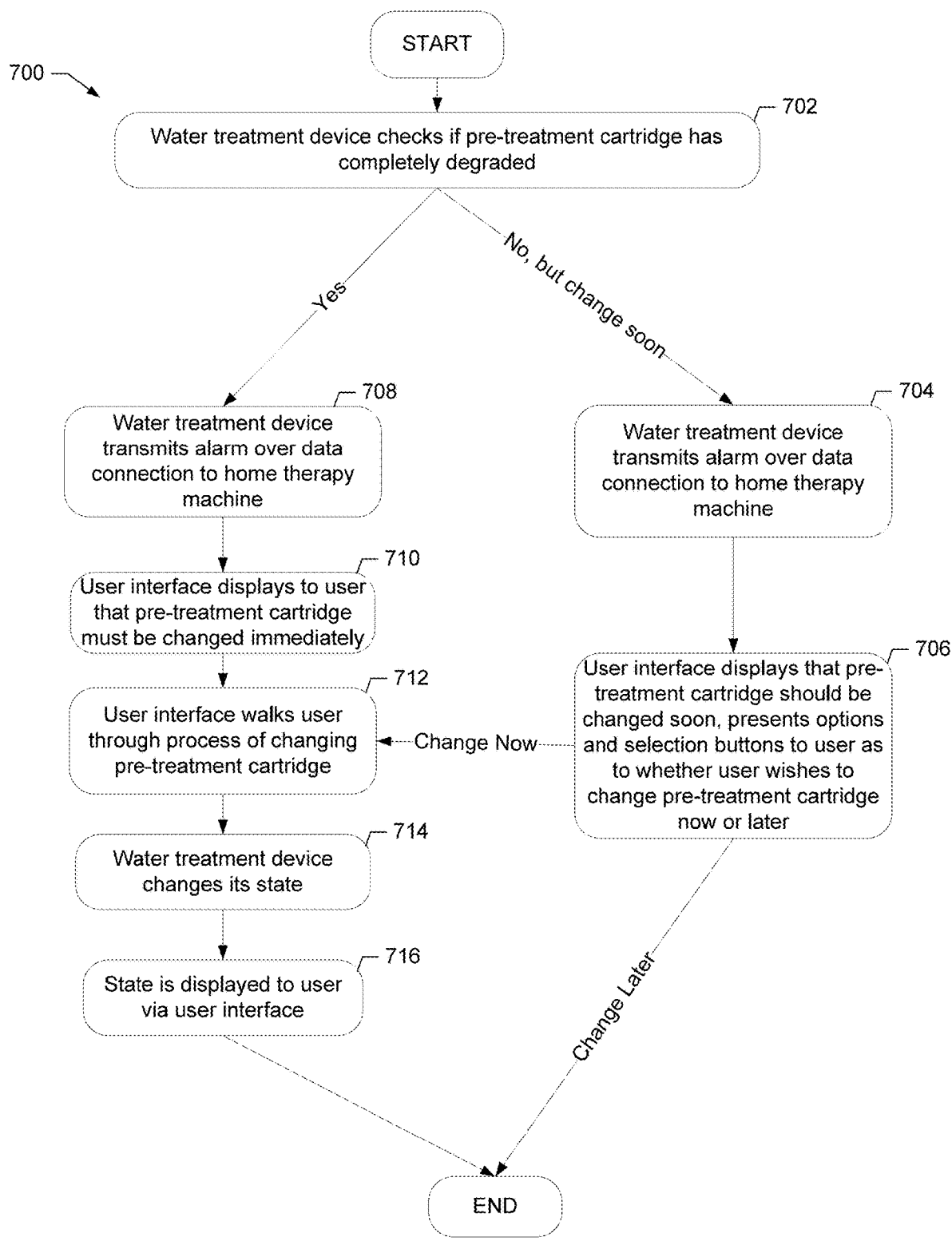
FIG. 7 is a flowchart of an example process of the present disclosure for updating a component in a water treatment device.

FIG. 7 illustrates an example process 700 for performing a pre-treatment cartridge swap in water treatment device 10 using user interface 112 of the home therapy machine 100. Upon starting process 700 at the start oval, water treatment device 10 checks whether the pre-treatment cartridge has completely degraded, as shown at block 702. If the pre-treatment cartridge has not completely degraded, but needs to be changed soon, the water treatment device 10 transmits an alarm over data connection 32 to the home therapy machine 100, as shown at block 704. User interface 122 displays that the pre-treatment cartridge should be changed soon and presents options and selection buttons to user 12 as to whether the user 12 wishes to change the pre-treatment cartridge now or later in one embodiment, as also shown at block 706. If the user selects, via user interface 122, to change the pre-treatment cartridge later, process 700 ends as illustrated at the end oval. If the user selects, via user interface 122, to change the pre-treatment cartridge now, process 700 proceeds to step 712, described below.

If the pre-treatment cartridge has completely degraded and needs to be changed immediately before water treatment device 10 can make water, water treatment device 10 transmits an alarm over data connection 32 to the home therapy machine 100, as shown at block 708, which causes user interface 122 to display to the user 12 that the pre-treatment cartridge must be changed immediately, as shown at block 710.

If the user 12 elects at user interface 122 to change the pre-treatment cartridge now (in the case in which the pre-treatment cartridge is not necessary), or the pre-treatment cartridge must be changed immediately, the user interface 122 in one embodiment walks user 12 through the process of changing the pre-treatment cartridge, as shown at block 712. Instructions for user tasks are displayed on the user interface 122. Once the pre-treatment cartridge swap is complete, water treatment device 10 changes its state, as shown at block 714, which is displayed to the user 12 via user interface 122, as shown at block 716. In various embodiments, process 700 may be used alternatively or additionally to perform an RO membrane swap. Process 700 then ends as illustrated at the end oval.

Setting Up and Using Supplies and Therapy Prescription

Medical products and drugs are shipped or delivered to a patient's home for the home therapy machine 100 to use during treatment. Typically, only therapy products or drugs approved under a doctor's prescription can be shipped to the patient's home. In the U.S., such prescriptions typically last one year, and patients may have more than one prescription available to them at any given time in order to dynamically manage their condition. One or more prescription is stored for each patient in the system hub 120. Each home therapy machine 100 uses supplies and settings according to the prescription. If the patient's prescription changes or if a prescription is added, the patient's clinician uses web portal 150 to update the settings of home therapy machine 100 to change or add the prescription. If the home therapy machine 100 settings are updated, system hub 120 sends the updated settings to home therapy machine 100 via the connectivity service as discussed previously, e.g., in one embodiment, the home therapy machine 100 only communicates with system hub 120 when connectivity agent 114 is turned on.

Figure 8:
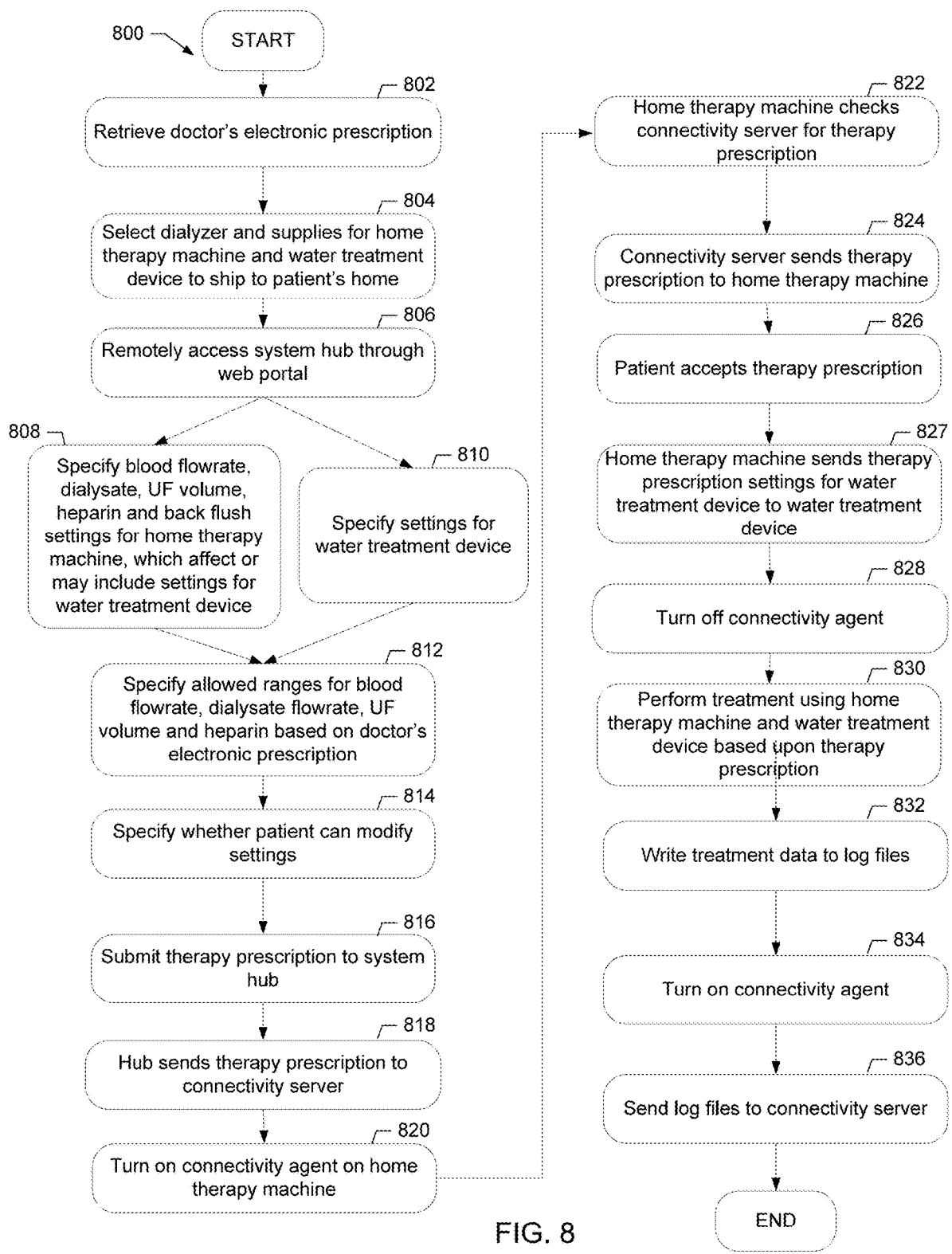
FIG. 8 is a flowchart of an example process of the present disclosure for shipping inventory and programming a therapy prescription for a home therapy machine and/or a water treatment device based upon an approved treatment prescription.

Referring now to FIG. 8, process 800 illustrates an example process for shipping inventory and programming a prescription for home therapy machine 100 based upon a doctor's prescription for a particular patient. That is, a doctor associated with the clinic 152$a$ to 152$n$ can also access system hub 120 via web portal 150 to deliver a therapy prescription for the patient (used for both supplies and machine operation) to the clinician. Upon starting process 800 at the start oval, the clinician retrieves an electronic prescription prescribed by a doctor using the web portal 150 as shown at block 802. At the web portal 150, the clinician selects the dialyzer, blood tubing set, acid, bicarbonate, needles, etc. and any other supplies, including possibly supplies for water treatment device 10, necessary to fulfill the prescription to run on home therapy machine 100. The selected dialyzer and other supplies will be shipped to the patient's home as shown at block 804.

At the same or different time, the clinician may remotely access the system hub 120 through the web portal 150 to program a prescription for home therapy machine 100, as shown at block 806. The system hub 120 holds the therapy prescription in one embodiment until the connectivity agent 114 on a home therapy machine 100 is turned on, as shown at blocks 820 to 824.

The clinician sets various treatment parameters used to program a prescription for the home therapy machine 100 as shown at block 808, such as blood flowrate, dialysate flowrate, UF volume and heparin flowrate flush. In one embodiment, the settings specified by the clinician include settings for operating the water treatment device 10 or may affect the parameters for water treatment device 10, as explained above, so separately setting parameters for water treatment device 10 is not necessary. Or, the clinician may separately set various treatment parameters used to program a prescription for the water treatment device 10, as shown at block 810.

The clinician also specifies allowed ranges for the various settings as shown at block 812. That is, the patient may be allowed to pick within a range of values for certain parameters under the specified therapy prescription. In this manner, the patient has a certain amount of control over the treatment that is performed. Dialysate temperature, for example, may be set within a range of allowable values based upon patient preference and comfort. The clinician further specifies whether or not the patient will have the ability to modify the settings at all as shown at block 814. If the patient is allowed to modify parameter settings, the setting variability is within an allowed range, such that the patient picks a value inside the range specified by the clinician at block 812. The clinician then submits the settings to the system hub 120 as shown at block 816.

The system hub 120 then sends the therapy prescription to the connectivity server 118 as shown at block 818. When the connectivity agent 114 residing at home therapy machine 100 is next turned on or enabled as shown at block 820, home therapy machine 100 checks the connectivity server 118 for a therapy prescription as shown at block 822. If a therapy prescription is present at the connectivity server 118 for the home therapy machine 100, connectivity server 118 sends the therapy prescription to the home therapy machine 100 as shown at block 824. Machine 100 prompts the patient to accept the therapy prescription. In one embodiment, the patient must accept the therapy prescription to continue using the home therapy machine 100, as shown at block 826.

In one embodiment, the therapy prescription downloaded from the connectivity server 118 may be a new or updated prescription, meant to replace a previous therapy prescription already on the machine 100. Before treatment begins, e.g., after disinfection the day before, ACPU 112 of home therapy machine 100 checks whether the connectivity service via agent 114 has posted an updated therapy prescription for that particular home therapy machine 100. To do so, in one embodiment, the home therapy machine 100 and the system hub 120, through the connectivity service, compare prescription version numbers to determine whether home therapy machine 100 has the most updated prescription. If not, the most recent prescription version is delivered to therapy machine 100. Machine 100 will not run an old therapy prescription if a new therapy prescription has been downloaded from connectivity server 118 and is present on machine 100. However, the new therapy prescription will not overwrite the old therapy prescription until the patient accepts the therapy prescription as shown at block 826. In this manner, the patient confirms that the patient knows that his or her treatment has changed. Upon accepting the new therapy prescription, the new therapy prescription is written into the memory of therapy machine 100. In an alternative embodiment, machine 100 can store multiple therapy prescriptions in memory so even when a new therapy prescription is downloaded, the old therapy prescription is kept in memory. Machine 100 may be able to store different types or categories of therapy prescriptions. Each different type of therapy prescription may provide a different treatment, e.g., to remove a low amount, medium amount, or large amount of ultrafiltration for dialysis. The machine 100 may be able to store one therapy prescription in each category.

ACPU 112 receives the settings and separates the home therapy machine 100 settings from the water treatment device 10 settings and sends the water treatment device 10 settings over the data connection 32 to the water treatment device 10, as shown at block 827. The settings may be flagged as being intended for the home therapy machine or the water treatment device 10. Or, the ACPU 112 may recognize characteristics in the settings as inherent to the water treatment device 10 and pass those settings to the water treatment device 10. The next time the patient is about to perform treatment, the connectivity agent 114 is turned off as shown at block 828. The home therapy machine 100 as shown at block 830 now runs a treatment using the therapy prescription specified at blocks 808 and/or 810. Home therapy machine 100 writes treatment data produced by the treatment to the log files as shown at block 832. Again, the log files document pertinent home therapy machine 100 data and pertinent water treatment device 10 data over the course of the treatment. In one embodiment, the water treatment device 10 sends its own log files to the home therapy machine 100. The home therapy machine 100 appends the data from the water treatment device 10 to the log files of the home therapy machine 100. The next time connectivity agent 114 is turned on, the combined log files stored in the home therapy machine 100 are sent to connectivity server 118.

Connectivity agent 114 is turned on as shown at block 834. In one embodiment, the home therapy machine 100 initiates the connection to the connectivity service. In an alternative embodiment, the connectivity service may initiate the connection to the home therapy machine 100. At block 836, the log files are uploaded to connectivity server 118. Process 800 then ends as illustrated at the end oval.

In one embodiment, machine 100 can perform post treatment procedures, such as a disinfection procedure that cleans the machine and the disposables used for treatment for the next treatment. In one embodiment, system 110 allows the connectivity agent to be turned on at block 834 after treatment but while post-treatment disinfection is taken place. Writing treatment data at block 832 can also be done during disinfection. Alternatively, the home therapy machine 100 waits to write data at block 832 or turn on the connectivity agent at block 834 until disinfection is completed and the machine 100 enters an idle mode.

In the illustrated embodiment, because the connectivity agent 114 turns off before treatment and does not turn on again until after treatment, system 110 provides no real-time monitoring of a treatment. Events that occur during a treatment, including alarms and alerts, are not reported to the system hub 120 immediately. Such information is part of the log files that are sent to the system hub 120 after treatment. In an alternative embodiment, the connectivity agent 114 may remain on during treatment and may report information about the home therapy machine 100 and the treatment in real-time.

Firmware Upgrades

From time to time, the software that ACPU 112 runs on home therapy machine 100 and/or the software that runs on processing and memory 24 on water treatment device 10, which may also be referred to herein as firmware, may need to be upgraded. The home medical device system 110 provides an efficient and reliable manner for upgrading firmware that integrates the product development team 128 and service personnel 132*a* to 132*n* (FIG. 1A).

Figure 9:
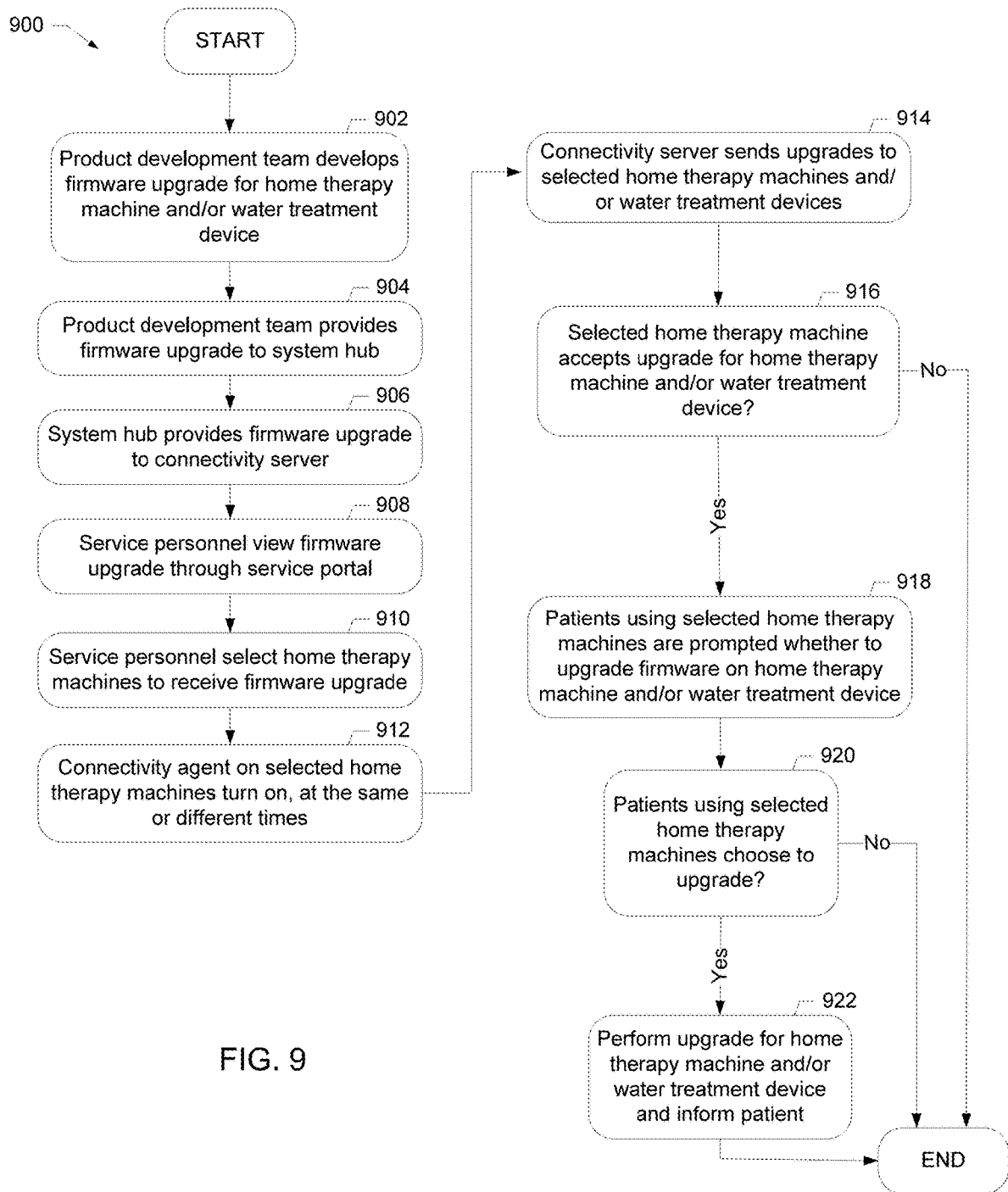
FIG. 9 is a flowchart of an example process of the present disclosure for upgrading firmware on a home therapy machine and/or a water treatment device.

FIG. 9 illustrates an example process 900 for upgrading firmware on the home therapy machine 100. Upon starting process 900 at the start oval, a product development team 128 develops a firmware upgrade for home therapy machine or water treatment device 10, as shown at block 902. At block 904, the product development team 128 uploads the firmware upgrade to the system hub 120. The service portal 130 then allows a service personnel director or decision-maker 134 to view and approve the upgrade. Upon approving the upgrade, director 134 uploads the upgrade from system hub 120 to the connectivity server 118, as shown at block 906. In the illustrated embodiment of FIG. 1A, director 134 is separate from the service personnel 132*a* to 132*n* that are responsible for servicing and maintaining home therapy machines 100 and water treatment devices 10, and for maintaining relationships with the patients. Service personnel director 134 not only has the authority to finalize whether the upgrade is sent to the connectivity server 118, director 134 can also designate which machines 100 and/or water treatment devices 10 receive the upgrade, if not all machines 100 or devices 10, and refuse the upgrade or return it to the product development team 128 for refinement. Once an upgrade is allowed to reach connectivity server 118, service personnel 132a to 132n, or designated ones thereof, can view the firmware upgrade through service portal 130 as illustrated at block 908. In one embodiment, the product development team 128 uploads the firmware upgrade directly to the connectivity server 118, without going through the system hub 120.

As discussed above in connection with FIG. 1A, service personnel 132a to 132n manage the day-to-day relationship with the patients. Service personnel 132a to 132n are familiar with patient schedules and are in the best position to determine when a patient should receive the firmware upgrade. For example, service personnel 132a to 132n will know the maintenance and activity schedule for the home therapy machines 100 and corresponding water treatment devices 10 that they normally service. If the patient's machine 100 and/or water treatment device 10 is scheduled to soon receive a part needed for the firmware upgrade, then the service personnel 132a to 132n can wait until the new part is installed before upgrading the firmware (which may, for example, need the new part) on the patient's home therapy machine 100 and/or water treatment device 10.

Each service personnel 132a to 132n selects which of its designated home therapy machines 100 and/or water treatment devices 10 should receive the firmware upgrade as shown at block 910. The next time connectivity agents 114 on the selected home therapy machines 100 are turned on, as shown at block 912, connectivity server 118, waiting for the agents to be turned on, sends the upgrade to the selected home therapy machines 100 and/or water treatment devices 10 as shown at block 914.

In one embodiment, the selected home therapy machines 100 and/or water treatment devices 10 may decide, based upon settings stored in the ACPU 112 and/or processing and memory 24, whether or not to accept the upgrade, as shown at block 916. If the selected home therapy machines 100 and/or water treatment devices 10 selects not to upgrade, process 900 ends as shown at block 916 and the end oval. If any of the selected home therapy machines 100 and/or water treatment devices 10 accept the upgrade, the corresponding patients are prompted via user interface 112 as to whether they would like to install the upgrade, as shown at block 918. If the patients, via user interface 112, do not choose to upgrade the selected home therapy machines 100 and/or water treatment devices 10, the process 900 ends as shown at block 920 and the end oval. If the patients, via user interface 112, choose to upgrade the selected home therapy machines 100 and/or water treatment devices 10, the upgrade(s) are performed, and the home therapy machines 100 inform the patients, via user interface 112 that the software has been upgraded as shown at block 922. Some countries require by law that patient approval must be obtained before upgrading a patient's firmware. In one embodiment, system 110 may require that only home therapy machines 100 in countries that require patient approval prompt patients to accept the firmware upgrade at blocks 918 and 920.

Home therapy machines 100 may be allowed to retain the ability to revert back to a previous software version for either or both of machine 100 or device 10. For example, if a firmware upgrade is corrupt, or if the firmware on a home therapy machine 100 or water treatment device 10 becomes corrupt, home therapy machine 100 in an embodiment is allowed to revert back to a previous, non-corrupt software version. Alternatively, home therapy machine 100 cannot revert back to a previous software version. Here, if the software is or becomes corrupted, new software is installed or home therapy machine 100 or water treatment device 10 is swapped with a new home therapy machine 100 or water treatment device 10.

The connectivity service at server 118 documents all events related to firmware upgrades, such as which patients have received upgrades, and which service personnel 132a to 132n have been involved in the upgrades. The connectivity server 118 stores serial numbers, tracking numbers and software versions so the various steps in the upgrade process are documented and so that at any given moment the current software version of each machine 100 and device 10 on system 110 can be readily obtained. At the end oval in FIG. 9, process 900 ends.

As discussed above, any software updates for the water treatment device 10 can also be sent to the water treatment device 10 through the home therapy machine 100. Home therapy machine 100 can receive a combined software upgrade that contains software upgrades for both the home therapy machine 100 and the water treatment device 10. Or, the upgrades can be delivered separately. The ACPU 112 then analyzes and separates the software contents for the home therapy machine 100 from the software contents for the water treatment device 10. In particular, the ACPU 112 can recognize which software contents are intended for the home therapy machine 100 and which software contents are intended for the water treatment device 10. For example, the software contents may inherently look or include content that is particular to either the home therapy machine 100 or the water treatment device 10. Or, the software content may be flagged as being for the home therapy machine 100 or the water treatment device 10. The home therapy machine 100 then sends the software contents for the water treatment device 10 over the data connection 32 to the water treatment device 10.

Firmware upgrades may additionally be provided in the manner described above for other home components of system 10, e.g., tablet 122, blood pressure monitor 104 and/or scale 106.

Clinician Dashboard with Rule-Evaluation

A clinician can view a list of the clinician's patients and a file for each patient showing how treatments for the patients have transpired. The treatment files are derived from the log files in the home therapy machine 100, including flowrates achieved, ultrafiltrate removal, ultrafiltration rates achieved, blood pressure over the course of therapy, weight, etc. The log files may also include treatment data for water treatment device 10 as described above. Stored treatment data for water treatment device 10 can include for example, total purified water volume delivered, average water temperature, average water pressure, number of delivery requests from machine 100, alerts and alarm information, chlorine/chloramines levels, and/or component use or replacement information.

A clinician can sort the list of patients by numerous categories, including the type of treatment they have received, e.g., hemodialysis (sub-categorized as for example short daily, nocturnal, every other day, and every other night), peritoneal dialysis (sub-categorized as continuous cycling peritoneal dialysis ("CCPD"), tidal, for example), the supervising doctor, or by the notifications described below. A clinician can also view a patient snapshot and an overview for the week, month or other duration.

Web portal 150 provides a clinician dashboard having notifications about events that occurred during treatment. In one embodiment, the notifications include colored flags, with different colors corresponding to different notification conditions. The clinicians can choose which events generate the red or yellow flags that appear on the dashboard. In one embodiment, the flag settings are clinic-specific, not patient-specific. Thus, choosing to be notified about certain events applies to all patients in the clinic or under the clinician's case. For example, a clinician may set a rule that a yellow flag should appear on the dashboard if a treatment lasted less than four hours. This rule would then apply to all patients at that clinic or under that clinician's care. The dashboard will indicate, e.g., with yellow flags, any patients who have undergone a treatment that lasted less than four hours. The flags may also pertain to water treatment device 10, e.g., post a flag when a disposable component of water treatment device 10 has less than ten hours of service left, or post a red flag if tested chlorine/chloramines reaches a certain level.

Figure 10A:
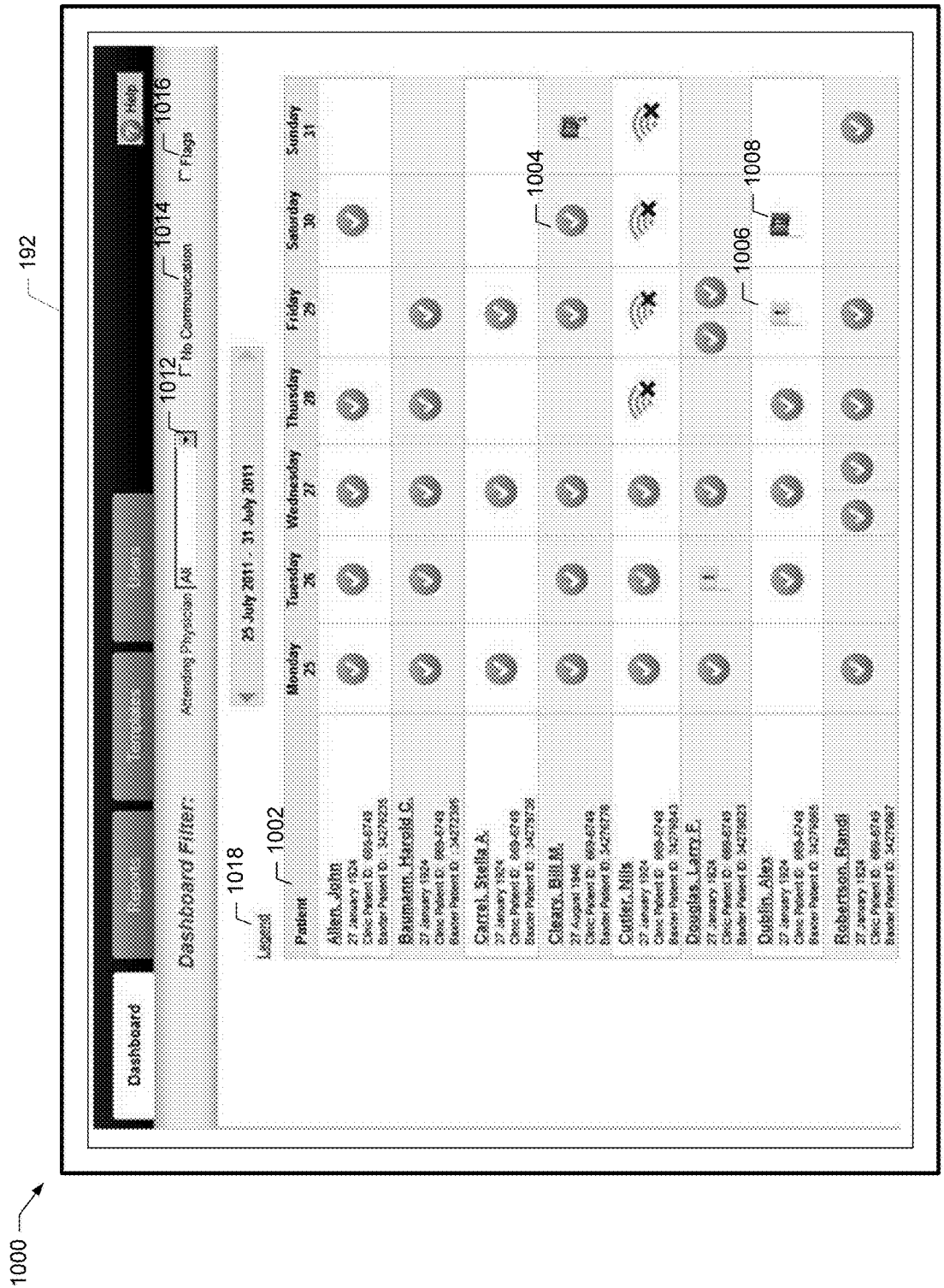
FIG. 10A is a screen shot of an example dashboard screen for a clinic of the present disclosure.

FIG. 10A illustrates an example dashboard screen 1000 for a clinic on a clinician's display device 192. Dashboard screen 1000 is in one implementation the first screen a clinician sees upon logging into the web portal 150. Dashboard screen 1000 provides an overview of information about the patients handled by that clinic, as well as how the treatments performed by home therapy machine 100 and water treatment device 10

The patients are listed by name as shown at column 1002. Dashboard 1000 may enable the clinician to apply filters as illustrated by drop down menu 1010. For example, the clinician in the illustrated embodiment can filter information in the dashboard by patient type (not shown), by physician at dropdown menu 1012, or by the status of a patient (not shown). The clinician can also filter information in the dashboard to only show treatments for which there has been no communication using checkbox 1014, or to only show treatments for which a flag has been generated using checkbox 1016. The filters allow the clinician to hone in on particular, desired information.

Various icons 1004, 1006 and 1008 indicate information about a treatment performed by that patient on a specific date. Icons 1004, 1006 and 1008 may indicate different types of events. For example, icon 1004 may be used to indicate that a treatment performed by the home therapy machine 100 and water treatment device 10 has been performed successfully. Icon 1006 may be used to notify the clinician about events that are not critical and do not need immediate action, but need to be closely monitored in the future. Icon 1008 for example may be used to notify the clinician of events that need immediate action.

Figure 10B:
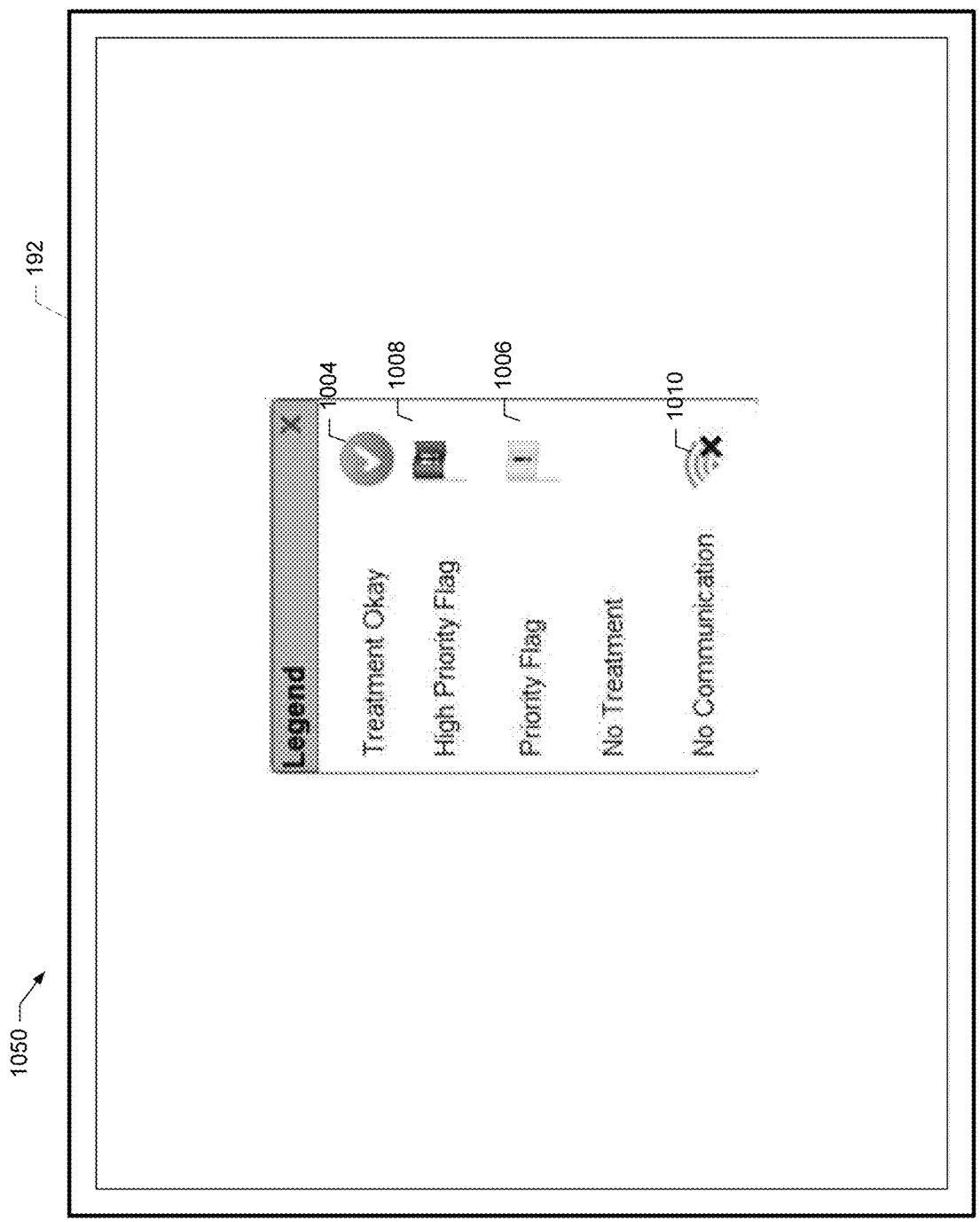
FIG. 10B is a screen shot of an example legend for a dashboard screen of the present disclosure.

A user is able to access a legend using link 1018. When a user selects link 1018, a popup window or new screen 1050 appears. FIG. 10B illustrates an example legend screen 1050 on a clinician's display device 192 that explains the various icons that can appear on dashboard screen 1000. Icon 1004 indicates that the treatment performed by home therapy machine 100 and water treatment device 10 went "Ok."Icon 1008 indicates a high priority flag. Icon 1006 indicates a flag of normal priority. Icon 1010 indicates that there has been no communication with the home therapy machine 100 associated with that patient for a specific treatment.

Figure 11A:
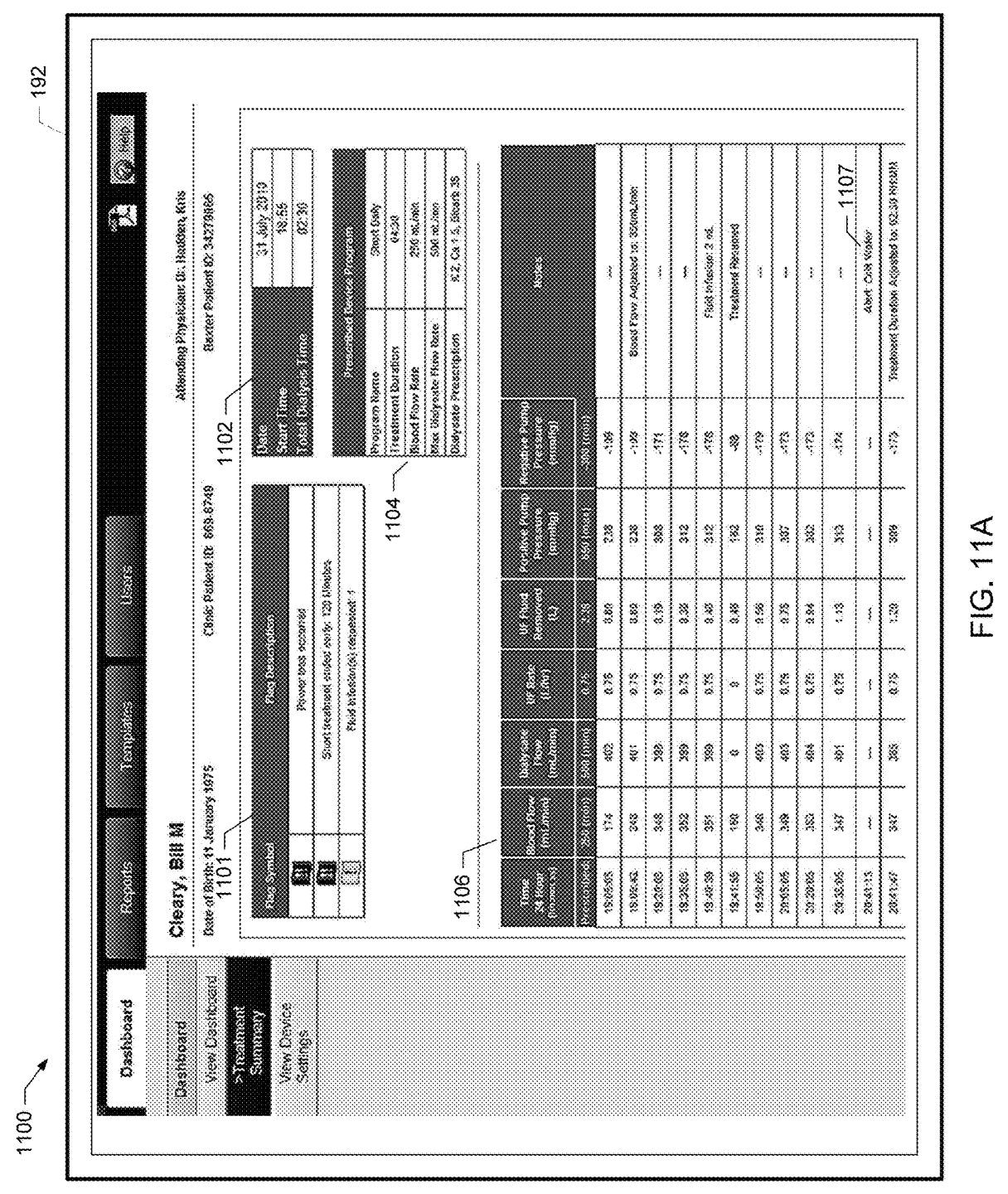

In one embodiment, the dashboard also displays information collected by the water treatment device 10 in the water treatment device 10 log files. FIG. 11A illustrates an example treatment summary screen 1100, which is part of the clinician dashboard or accessible via a link from the dashboard, on a clinician's display device 192. Treatment summary screen 1100 provides granulated details about a particular treatment performed on a patient by home therapy machine 110 and water treatment device 10 as collected in the log files as described above. FIG. 11A shows information about a treatment performed by home therapy machine 100 and water treatment device 10 on Jul. 31, 2010, as indicated at chart 1102. From treatment summary screen 1100, a clinician can see a description of the flag symbols at chart 1101. The clinician can also view the date, start time and total dialysis time at chart 1102, the prescribed device program at chart 1104 and overall treatment summary log in table format showing exact times for various treatment events for home therapy machine 100 and/or water treatment device 10 at chart 1106. The treatment summary screen 1100 also indicates information collected from water treatment device 10. For example, item 1107 in chart 1106 indicates to a clinician that water treatment device 10 registered a cold water alert at time 20:41:13. Any of the alerts or events documented in the log files and displayed on the clinician dashboard may also have been communicated to the user 12 via user interface 122 during the therapy at the time the alert or event occurred.

Figure 11B:
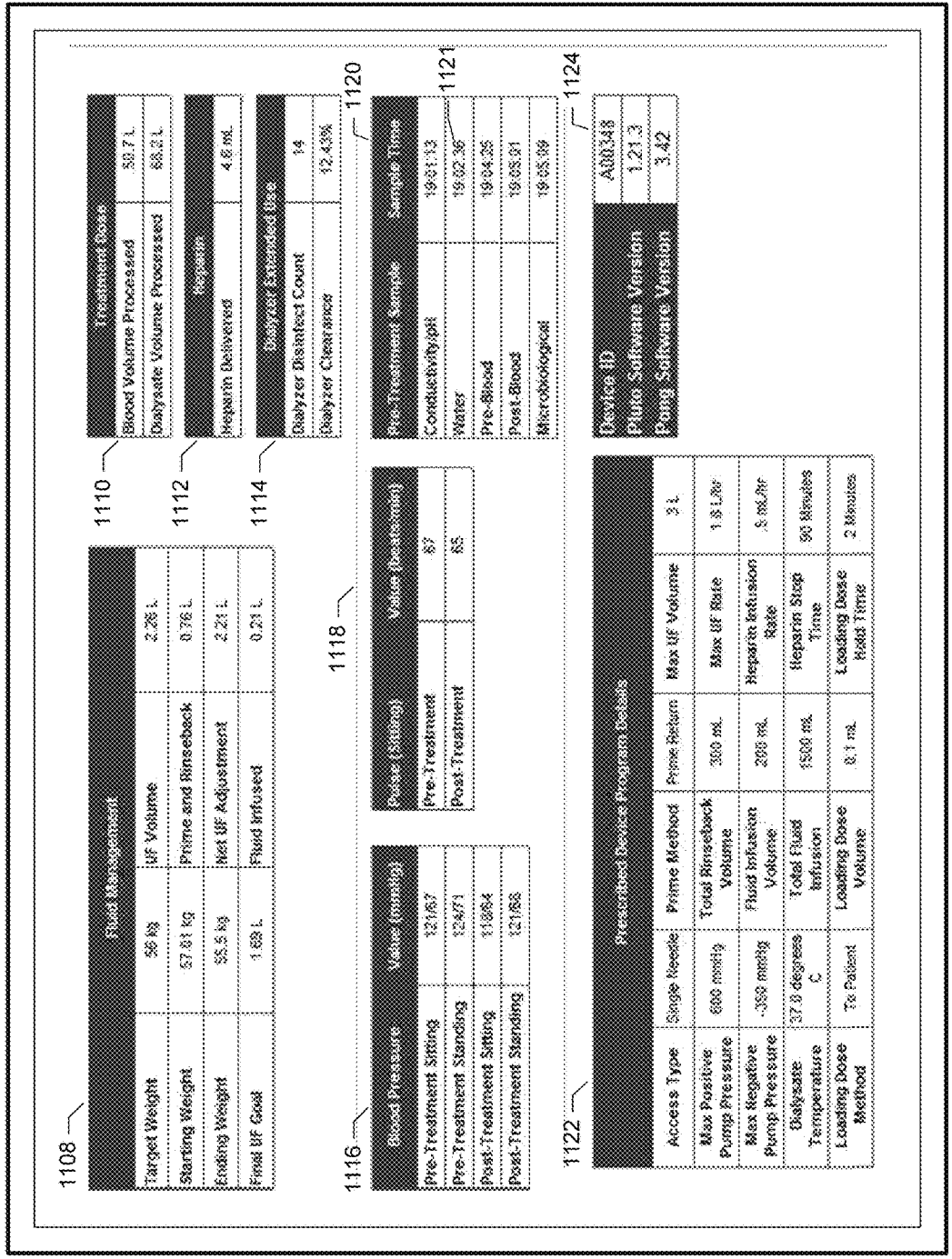
FIG. 11B is another screen shot of an example treatment summary screen of the present disclosure.

The screen 1100, displayed on a clinician's display device 192, is continued on FIG. 11B. As shown in FIG. 11B, a clinician can view fluid management particulars at chart 1108, information about the treatment dose at chart 1110, heparin particulars at chart 1112, dialyzer extended use data at chart 1114, blood pressure at chart 1116, and pulse particulars at chart 1118. A clinician can also view information about pretreatment samples taken for comparison purposes at chart 1120, including the time 1121 that a water sample was taken from water treatment device 10. A clinician can also view details about the prescribed device program at chart 1122. The clinician can also view the device ID of the home therapy machine 100 and the software versions of the home therapy machine 100 as well as the water treatment device 10 at chart 1124.

Figure 12:
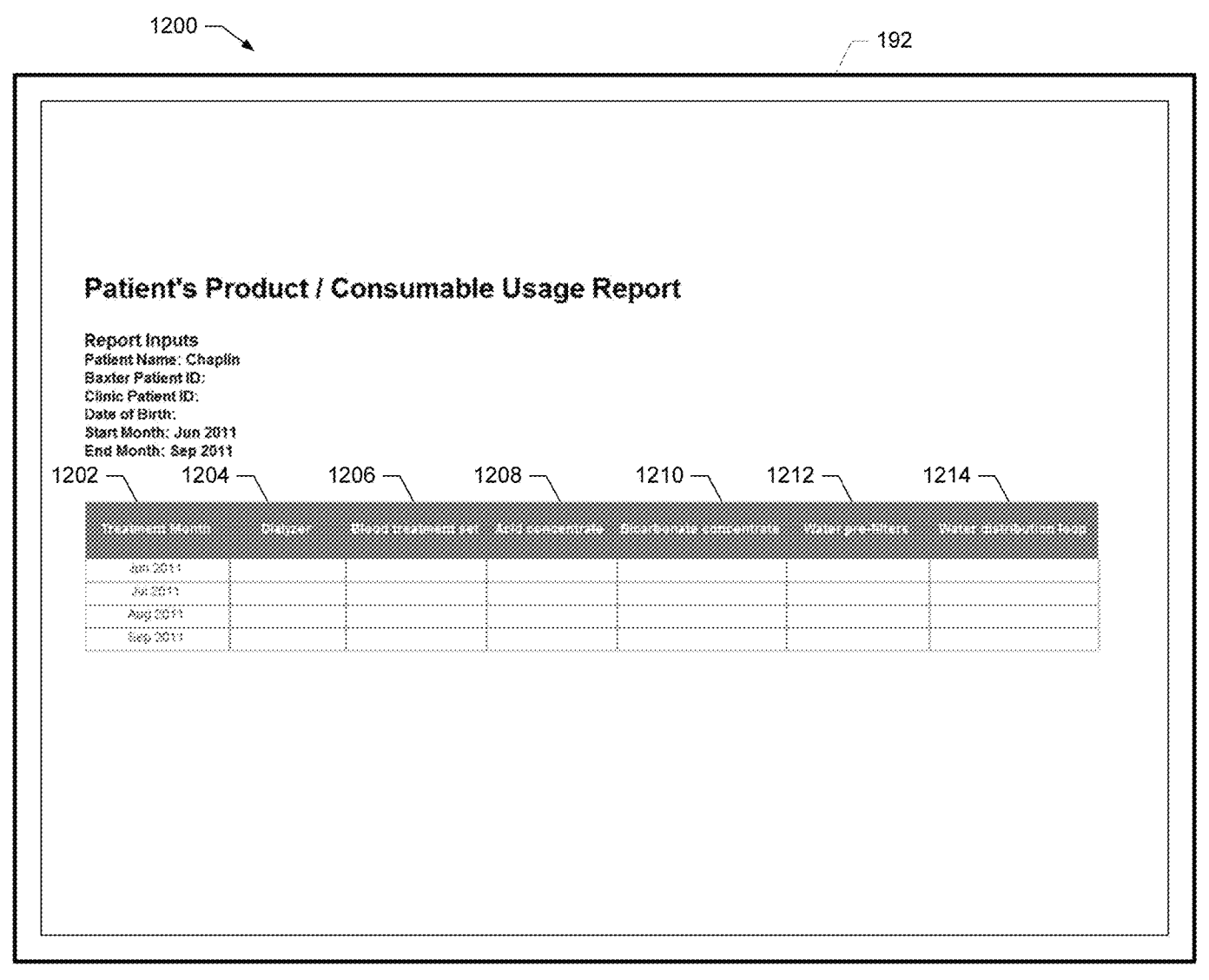

FIG. 12 illustrates an example patient usage report 1200 that may be presented to a clinician at web portal 150 on a clinician's display device 192. The example patient usage report 1200 allows a clinician to view the amount of product or consumables utilized by home therapy machine 100 and water treatment device 10 in treating a specific patient over a specified time frame. In the patient usage report 1200, the clinician can view the treatment month 1202 as well as information relating to usage by home therapy machine 100, such as the dialyzer used 1204, the blood treatment set used 1206, the acid concentrate used 1208 and the bicarbonate concentrate used 1210. The clinician can also view information relating to usage by water treatment device 10, such as the water pre-filters used 1212 and the water distribution loop used 1214. Thus, the clinician can view information about the usage of consumables over one or several treatments that relate to the home therapy machine 100 as well as the water treatment device 10.

Additional Aspects of the Present Disclosure

Aspects of the subject matter described herein may be useful alone or in combination with any one or more of the other aspect described herein. Without limiting the foregoing description, in a first aspect of the present disclosure, a home medical device system includes a home therapy machine for performing a home therapy on a patient; a user interface operably connected to the home therapy machine, the user interface receiving operator inputs; a water treatment device in fluid communication with the home therapy machine; and a data connection between the home therapy machine and the water treatment device, wherein the home therapy machine transmits data via the connection to the water treatment device for control of the water treatment device, the data provided based on at least one of the operator inputs received via the user interface.

In accordance with a second aspect of the present disclosure, which may be used in combination with any one or more of the preceding aspects, the water treatment device transmits to the home therapy machine at least one of: (i) state information, (ii) component life information, (iii) self test results, (iv) alert information or (v) version information.

In accordance with a third aspect of the present disclosure, which may be used in combination with any one or more of the preceding aspects, the user interface displays at least one of: (i) the state information, (ii) the component life information, (iii) the self test results, (iv) the alert information or (v) the version information.

In accordance with a fourth aspect of the present disclosure, which may be used in combination with any one or more of the preceding aspects, the home therapy machine transmits to the water treatment device at least one of: (i) state change requests, (ii) status queries, (iii) flowrate change requests, (iv) software upgrades or downgrades, or (v) file transfers.

In accordance with a fifth aspect of the present disclosure, which may be used in combination with any one or more of the preceding aspects, wherein the user interface displays at least one of: (i) the state change requests, (ii) the status queries, (iii) the flowrate change requests, (iv) the software upgrades or downgrades, or (v) the file transfers.

In accordance with a sixth aspect of the present disclosure, which may be used in combination with any one or more of the preceding aspects, the at least one operator input leading to the transmitted data concerns a water treatment device parameter.

In accordance with a seventh aspect of the present disclosure, which may be used in combination with any one or more of the preceding aspects, the at least one operator input leading to the transmitted data concerns a home therapy machine parameter, the transmitted data an automatic result of a change in the home therapy machine parameter.

In accordance with an eighth aspect of the present disclosure, which may be used in combination with any one or more of the preceding aspects, a home therapy medical system includes a home therapy machine for performing a home therapy on a patient; a user interface operably connected to the home therapy machine, the user interface receiving operator inputs; a water treatment device in fluid communication with the home therapy machine; a server in data flow communication with the home therapy machine; and a data connection between the home therapy machine and the water treatment device, wherein the home therapy machine transmits data via the connection to the water treatment device, the data based on a therapy prescription sent from the server to the home therapy machine.

In accordance with a ninth aspect of the present disclosure, which may be used in combination with any one or more of the preceding aspects, the transmitted data is for control of the water treatment device.

In accordance with a tenth aspect of the present disclosure, which may be used in combination with any one or more of the preceding aspects, the therapy prescription specifies the data transmitted from the home therapy machine to the water treatment device.

In accordance with an eleventh aspect of the present disclosure, which may be used in combination with any one or more of the preceding aspects, the therapy prescription specifies an operating parameter for the home therapy machine, the transmitted data based on the specified operating parameter.

In accordance with a twelfth aspect of the present disclosure, which may be used in combination with any one or more of the preceding aspects, the home therapy machine determines the transmitted data based on the specified operating parameter.

In accordance with a thirteenth aspect of the present disclosure, which may be used in combination with any one or more of the preceding aspects, the water treatment device uses the data to determine a corresponding operating parameter for the water treatment device.

In accordance with a fourteenth aspect of the present disclosure, which may be used in combination with any one or more of the preceding, the server is configured to send a software upgrade to the home therapy machine, the software upgrade if meant for the water treatment device forwarded by the home therapy machine to the water treatment device.

In accordance with a fifteenth aspect of the present disclosure, which may be used in combination with any one or more of the preceding aspects, the software upgrade is automatically installed on the water treatment device or installed upon acceptance by a user via the user interface.

In accordance with a sixteenth aspect of the present disclosure, which may be used in combination with any one or more of the preceding aspects, the server is in data communication with a service computer, the service computer enabling a service person to access the water treatment device via the data connection with the home therapy machine to perform at least one service procedure.

In accordance with a seventeenth aspect of the present disclosure, which may be used in combination with any one or more of the preceding aspects, upon startup, the home therapy machine is configured to determine if the water treatment device is in a hibernation mode and if so to perform a startup procedure not involving the water treatment device.

In accordance with an eighteenth aspect of the present disclosure, which may be used in combination with any one or more of the preceding aspects, the home therapy medical system is configured to enable a user via the user interface to run at least one self test for the home therapy machine and at least one self test for the water treatment device.

In accordance with a nineteenth aspect of the present disclosure, which may be used in combination with any one or more of the preceding aspects, a home therapy medical system includes a home therapy machine for performing a home therapy on a patient; a user interface operably connected to the home therapy machine, the user interface receiving operator inputs; a water treatment device in fluid communication with the home therapy machine; a server in data flow communication with the home therapy machine; and a data connection device between the home therapy machine and the water treatment device, wherein the water treatment device is configured to transmit data via the data connection to the home therapy machine, which forwards the data to the server.

In accordance with a twentieth aspect of the present disclosure, which may be used in combination with any one or more of the preceding aspects, the transmitted data includes treatment log data.

In accordance with a twenty-first aspect of the present disclosure, which may be used in combination with any one or more of the preceding aspects, the transmitted data includes component usage or component replacement data.

In accordance with a twenty-second aspect of the present disclosure, any of the structure and functionality illustrated and described in connection with FIG. 1 may be used in combination with any one or more of the preceding aspects.

In accordance with a twenty-third aspect of the present disclosure, any of the structure and functionality illustrated and described in connection with FIG. 1A may be used in combination with any one or more of the preceding aspects.

In accordance with a twenty-fourth aspect of the present disclosure, any of the structure and functionality illustrated and described in connection with FIG. 2 may be used in combination with any one or more of the preceding aspects.

In accordance with a twenty-fifth aspect of the present disclosure, any of the structure and functionality illustrated and described in connection with FIG. 3 may be used in combination with any one or more of the preceding aspects.

In accordance with a twenty-sixth aspect of the present disclosure, any of the structure and functionality illustrated and described in connection with FIG. 4 may be used in combination with any one or more of the preceding aspects.

In accordance with a twenty-seventh aspect of the present disclosure, any of the structure and functionality illustrated and described in connection with FIG. 5 may be used in combination with any one or more of the preceding aspects.

In accordance with a twenty-eighth aspect of the present disclosure, any of the structure and functionality illustrated and described in connection with FIG. 6 may be used in combination with any one or more of the preceding aspects.

In accordance with a twenty-ninth aspect of the present disclosure, any of the structure and functionality illustrated and described in connection with FIG. 7 may be used in combination with any one or more of the preceding aspects.

In accordance with a thirtieth aspect of the present disclosure, any of the structure and functionality illustrated and described in connection with FIG. 8 may be used in combination with any one or more of the preceding aspects.

In accordance with a thirty-first aspect of the present disclosure, any of the structure and functionality illustrated and described in connection with FIG. 9 may be used in combination with any one or more of the preceding aspects.

In accordance with a thirty-second aspect of the present disclosure, any of the structure and functionality illustrated and described in connection with FIG. 10A may be used in combination with any one or more of the preceding aspects.

In accordance with a thirty-third aspect of the present disclosure, any of the structure and functionality illustrated and described in connection with FIG. 10B may be used in combination with any one or more of the preceding aspects.

In accordance with a thirty-fourth aspect of the present disclosure, any of the structure and functionality illustrated and described in connection with FIG. 11A may be used in combination with any one or more of the preceding aspects.

In accordance with a thirty-fifth aspect of the present disclosure, any of the structure and functionality illustrated and described in connection with FIG. 11B may be used in combination with any one or more of the preceding aspects.

In accordance with a thirty-sixth aspect of the present disclosure, any of the structure and functionality illustrated and described in connection with FIG. 12 may be used in combination with any one or more of the preceding aspects.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis system comprising:
   a water treatment device including a water treatment processor, the water treatment device fluidly connected to a water source and configured to provide purified water; and
   a dialysis machine including a dialysis machine processor, a dialysate holding tank, and at least one dialysate mixing pump connected to a source of concentrate, the dialysis machine processor communicatively coupled to the water treatment processor for preparing dialysate using the purified water provided by the water treatment device, wherein the dialysis machine processor is configured to:
   receive an indication that a batch of dialysate is needed,
   transmit a first message to the water treatment processor to begin providing the purified water,
   cause the at least one dialysate mixing pump to pump a concentrate from the source of concentrate for mixing with the purified water to form the dialysate for storage in the dialysate holding tank, and
   after the batch of the dialysate has been stored in the dialysate holding tank, transmit a second message to the water treatment processor to stop providing the purified water.

2. The dialysis system of claim 1, wherein the indication that the batch of the dialysate is needed includes determining that a volume of the dialysate within the dialysate holding tank is below a certain low level.

3. The dialysis system of claim 1, wherein the dialysis machine processor is further configured to:
   determine or receive an indication that the dialysate within the dialysate holding tank has reached a certain high level; and
   transmit the second message after determining or receiving the indication that the dialysate within the dialysate holding tank has reached the certain high level.

4. The dialysis system of claim 1, wherein the indication that the batch of the dialysate is needed includes a detected time of use for a dialysis treatment.

5. The dialysis system of claim 1, wherein the first message includes an indication of a flow rate for the purified water.

6. The dialysis system of claim 5, wherein the dialysis machine processor is further configured to:
   determine a higher rate of production for the dialysate is needed; and
   transmit another first message to the water treatment processor indicative of a higher, second flow rate for the purified water.

7. The dialysis system of claim 6, wherein the dialysis machine processor is further configured to cause the at least one dialysate mixing pump to pump the concentrate from the source of concentrate at a faster rate for mixing with the purified water to form the dialysate for storage in the dialysate holding tank.

8. The dialysis system of claim 5, wherein the flow rate for the purified water is determined by the dialysis machine processor as being proportional to dialysate fluid flow rate or dialysis fluid demand.

9. The dialysis system of claim 1, wherein the dialysis machine further includes a user interface for receiving the indication that the batch of the dialysate is needed.

10. The dialysis system of claim 1, wherein the dialysis machine includes at least one of a hemodialysis machine, a peritoneal dialysis machine, a hemofiltration machine, or a hemodiafiltration machine.

11. The dialysis system of claim 1, wherein the water source includes an online water source and the purified water has a purity corresponding to an injectable quality or a sterile quality.

12. The dialysis system of claim 1, wherein the concentrate includes dextrose or glucose concentrate.

13. A dialysis system comprising:
a water treatment device including a water treatment processor, the water treatment device fluidly connected to a water source and configured to provide purified water; and
a dialysis machine including a dialysis machine processor, a dialysate holding tank, and at least one dialysate mixing pump connected to a source of concentrate, the dialysis machine processor communicatively coupled to the water treatment processor for preparing dialysate using the purified water provided by the water treatment device, wherein the dialysis machine processor is configured to:
receive an indication that a batch of dialysate is needed,
transmit a message to the water treatment processor indicative of needed volume of purified water, and
cause the at least one dialysate mixing pump to pump a concentrate from the source of concentrate for mixing with the purified water to form the dialysate for storage in the dialysate holding tank,
wherein the water treatment processor is configured to stop providing the purified water to the dialysis machine when the needed volume of purified water has been reached.

14. The dialysis system of claim 13, wherein the indication that the batch of the dialysate is needed includes determining that a volume of the dialysate within the dialysate holding tank is below a certain low level.

15. The dialysis system of claim 13, wherein the indication that the batch of the dialysate is needed includes a detected time of use for a dialysis treatment.

16. The dialysis system of claim 13, wherein the dialysis machine further includes a user interface for receiving the indication that the batch of the dialysate is needed.

17. The dialysis system of claim 13, wherein the message includes an indication of a flow rate for the purified water, and
wherein the dialysis machine processor is further configured to:
determine a higher rate of production for the dialysate is needed; and
transmit another message to the water treatment processor indicative of a higher, second flow rate for the purified water.

* * * * *